(12) United States Patent
Scott et al.

(10) Patent No.: US 11,896,801 B2
(45) Date of Patent: Feb. 13, 2024

(54) KINKLESS INFUSION SET FOR MEDICAL USE

(71) Applicants: Mark H Scott, San Diego, CA (US);
Leif Bowman, San Diego, CA (US);
Nicholas John Foley, Edinburgh (GB)

(72) Inventors: Mark H Scott, San Diego, CA (US);
Leif Bowman, San Diego, CA (US);
Nicholas John Foley, Edinburgh (GB)

( * ) Notice: Subject to any disclaimer, the term of this patent is extended or adjusted under 35 U.S.C. 154(b) by 0 days.

(21) Appl. No.: 16/714,701

(22) Filed: Dec. 14, 2019

(65) Prior Publication Data

US 2021/0178058 A1    Jun. 17, 2021
US 2023/0132398 A9    Apr. 27, 2023

Related U.S. Application Data

(60) Provisional application No. 62/780,231, filed on Dec. 15, 2018.

(51) Int. Cl.
| | |
|---|---|
| *A61M 5/158* | (2006.01) |
| *A61M 5/168* | (2006.01) |
| *A61M 5/46* | (2006.01) |
| *A61M 5/142* | (2006.01) |

(52) U.S. Cl.
CPC ........ *A61M 5/158* (2013.01); *A61M 5/16813* (2013.01); *A61M 5/16877* (2013.01); *A61M 5/46* (2013.01); *A61M 5/142* (2013.01); *A61M 2005/1585* (2013.01); *A61M 2005/1586* (2013.01); *A61M 2205/3303* (2013.01); *A61M 2230/201* (2013.01)

(58) Field of Classification Search
None
See application file for complete search history.

(56) References Cited

U.S. PATENT DOCUMENTS

| | | | |
|---|---|---|---|
| 7,611,492 B2 * | 11/2009 | Sonoda | A61B 17/3403 604/159 |
| 8,323,250 B2 * | 12/2012 | Chong | A61L 27/28 604/180 |
| 2008/0312600 A1 * | 12/2008 | Krulevitch | A61M 5/158 604/181 |
| 2013/0253532 A1 | 9/2013 | Fueglister | |
| 2016/0213838 A1 | 7/2016 | Schabbach | |

(Continued)

FOREIGN PATENT DOCUMENTS

| | | |
|---|---|---|
| CN | 101 631 585 B | 10/2013 |
| CN | 101631585 B | 10/2013 |

OTHER PUBLICATIONS

Supplementary European Search Report.

*Primary Examiner* — Laura A Bouchelle

(57) ABSTRACT

Briefly, a kinkless infusion set has a setting control that engages a curved or helical cannula to simultaneously rotate the helical cannula as the helical cannula is moved toward a patients skin and then under the patient's skin to position the curved or helical cannula to a desired depth and position. In one example, the helical cannula is set between 3 mm and 5 mm under the patient's skin. Also, the curved or helical cannula may have side ports to allow medicine to be presented over a larger area for more effective therapeutic treatment. In some constructions the patient rotates the setting control, and in other cases the patient may push, pull or translate the setting control.

20 Claims, 19 Drawing Sheets

(56) References Cited

U.S. PATENT DOCUMENTS

2016/0213840 A1    7/2016  Schabbach
2018/0207356 A1*  7/2018  Joseph .............. A61M 39/0247
2018/0280608 A1*  10/2018  Gillett ............... A61M 5/14248

* cited by examiner

KINKLESS INFUSION SET FOR MEDICAL USE

RELATED APPLICATIONS

This application claims priority to U.S. provisional application No. 62/780,231, filed Dec. 15, 2019, and entitled "Kinkless Infusion Set." This application is related to U.S. patent application Ser. No. 16/560,315, filed Sep. 9, 2019, and entitled "Extended Use Infusion Set for Medical Use," which is incorporated herein by reference.

FIELD OF THE INVENTION

This invention relates to infusion sets for delivering therapeutics and medicines into the body of a mammal, including humans. More particularly, the invention relates to structures and processes for inserting a cannula or needle subcutaneously using a setting mechanism such that the cannula or needle can be positioned without kinking the setting tube.

BACKGROUND OF THE INVENTION

Millions of people in the United States and around the world suffer from diseases that require the infusion of medicines, therapeutics, or biologics over extended periods of time. For example, millions of people just in the United States suffer from diabetes and require insulin continually to just stay alive and have an opportunity for a normal life. For some, regular injections are sufficient, however many may benefit from continuous monitoring and delivery of insulin. These people wear a continuous glucose monitor for monitoring their glucose levels, which provides information which can drive or can inform the user to adjust a pump that delivers insulin into their system through an infusion set. It may also suggest they inject a bolus (larger single dose) or that they should eat. In this way, the patient can maintain a more constant blood glucose level, avoid dangerous highs and lows in glucose levels, and have the best opportunity for a normal and comfortable life. Further, many people who currently use needle injections could benefit from a more continuous treatment that can be provided through continuous glucose monitoring, pumps, and infusion sets. However, due to their cost, inconvenience, and pain, many people who could benefit do not use continuous glucose monitors, infusion pumps, and infusion sets.

Although the disclosures herein regarding infusion sets will focus on using infusion sets for primarily insulin delivery, it will be understood that similar benefits may be achieved for other types of medicines, therapeutics, and biologics.

Current infusion sets suffer from several deficiencies. Most often, a patient is trained to attach the infusion set to their body. Often this can be an involved and complicated process, and often the patient must try several times to get infusion set to be properly attached for delivering medicine. This can be painful, and also expensive as sometimes multiple attempts will destroy the infusion set.

Once installed and in operation, infusion sets typically have a duration of only 1-3 days before it is necessary to remove the infusion set and find a new location on the body. Since infusion sets are designed for a single use, each time the infusion set is removed, the patient is required to purchase and attach a new infusion set. The result is patients needing between 100+ to 300+ disposable infusion sets annually. In this way, the decision to move from injection-based insulin to continuous-based insulin delivery can involve a significant and oftentimes prohibitive expense, despite its therapeutic benefits to the patient.

Unfortunately, current infusion sets provide substantially reduced therapeutic benefit after the first 24 hours. That is, after 24 hours, the effectiveness of the medication delivery is reduced, thereby requiring an increased dosage of the medication, or potentially having the patient not receive a full therapeutic and beneficial effect. Many factors affect how long an infusion set will give therapeutic effect. For example, whether or not the cannula was properly installed, the depth that the cannula was installed under the skin, whether the cannula was or became damaged or kinked under the skin or outside of the body, and the physical activity of the patient. Further, it has been found that the tissue changes at the point in which medicine is delivered and becomes resistant to further delivery. There may be hardening of the tissue around the end of the needle or cannula, biological responses such as macrophages, crystallization of the infusion fluid in or around the infusion cannula, or other biological changes such that the backpressure on the fluid increases. There may be changes in the fluid absorption capacity of the tissue at the position of greatest fluid transfer, even without a sensation that may be described as hardening, that decrease the effectiveness of the fluid medicine to achieve its therapeutic benefits.

An infusion set delivers medicine into the body through a cannula, that is essentially a thin flexible tube for delivering medicine to a particular depth and position under the skin. However, this cannula is too soft and flexible to penetrate the skin and be pushed to the therapeutic location. Accordingly, infusion sets use an introducer needle that extends through the cannula and is used to pierce the skin and forge the path through patient tissue to the therapeutic location. Once the cannula is in a proper position, the introducer needle is removed and discarded, along with any insertion mechanism. In some cases, the insertion mechanism is reusable instead of disposable.

The current state of the art for infusion sets uses an introducer needle with a soft cannula around it for the length of the needle that penetrates the skin. The end of the soft cannula is formed onto the surface of the introducer needle to ensure a tight fit that can withstand the forces of insertion through the skin. As the introducer needle usually has a beveled edge to create a sharp point or edge to penetrate the skin, it is necessary for the introducer needle to protrude approximately 3 mm beyond the end of the soft cannula. The result is that a patient who requires a soft cannula tip to deliver medication into the body at a depth of 6 mm must insert the introducer need 9 mm deep. Such a deep insertion creates a deeper wound and more pain than necessary and is additionally intimidating to the user.

Further, the introducer needles used in the current infusion sets are seen by the user upon removal, and this view of the needle is intimidating to the user and reinforces the negative aspect of inserting infusion sets.

Also, during the insertion process current infusion sets are prone to having the cannula kink during the insertion process, which can interfere with setting the cannula to the proper depth and location for effective infusion, or the kink may restrict the flow of medicine into the patient. If the patient recognizes the cannula has kinked, the patient likely has to throw the kinked infusion set away, and start again with a new expensive replacement infusion set. Worse, if the cannula is kinked, but the patient is unaware, then the patient will not receive a proper therapeutic level of medicine, which can lead to dangerous glucose blood levels. Accordingly, there is a need for a reliable setting mechanism to insert a cannula with a substantially reduced risk of the cannula kinking during the insertion process.

SUMMARY

A kinkless infusion set is disclosed that has a setting control that engages a helical cannula to simultaneously rotate the helical cannula as the helical cannula is moved toward a patients skin and then under the patient's skin to position the helical cannula to a desired depth and position. In one example, the helical cannula is set between 3 mm and 5 mm under the patient's skin. Also, the helical cannula may have side ports to allow medicine to be presented over a larger area for more effective therapeutic treatment. In some constructions the patient rotates the setting control, and in other cases the patient may push, pull or translate the setting control.

In one example, the setting control is a disk that the patient first exposes, and then rotates, which rotates a gear that is set against a rack. As the gear rotates, the rack translates, which causes a second gear to rotate, and due to the bias in the gear teeth and rack, the gear is simultaneously moved toward the patient's skin. The helical cannula is connected to the second gear, and is thereby moved from its initial storage position, through the patient's skin, and finally to its intended depth and position. There are many alternatives to such a rack and pinion system consistent with this disclosure.

In another aspect, the setting control may be connected to variable gearing such that the rotating and moving of the helical cannula is relatively faster when it is being moved from its storage position, but then slows as it reaches and penetrates the patient's skin. In this way, the patient has increased control over the cannula as it is under his or her skin, with a more comfortable insertion.

Advantageously, the correlated and simultaneous rotation and translation of the helical cannula enables the cannula to be fully inserted with a very low likelihood of kinking.

The kinkless infusion set may also be advantageously used with biosensors, such as sensors for detecting blood glucose levels. Similar to setting a cannula, the kinkless set may be used to set and reset a biosensor for extended sensing. In some cases, a biosensor and cannula may be used at the same time, for example through two available ports, and other times the biosensor may be used to replace the cannula.

BRIEF DESCRIPTION OF THE DRAWINGS

These and other objects and advantages of the invention will become apparent upon reading the following detailed description and upon referring to the drawings and claims.

Figure 1:
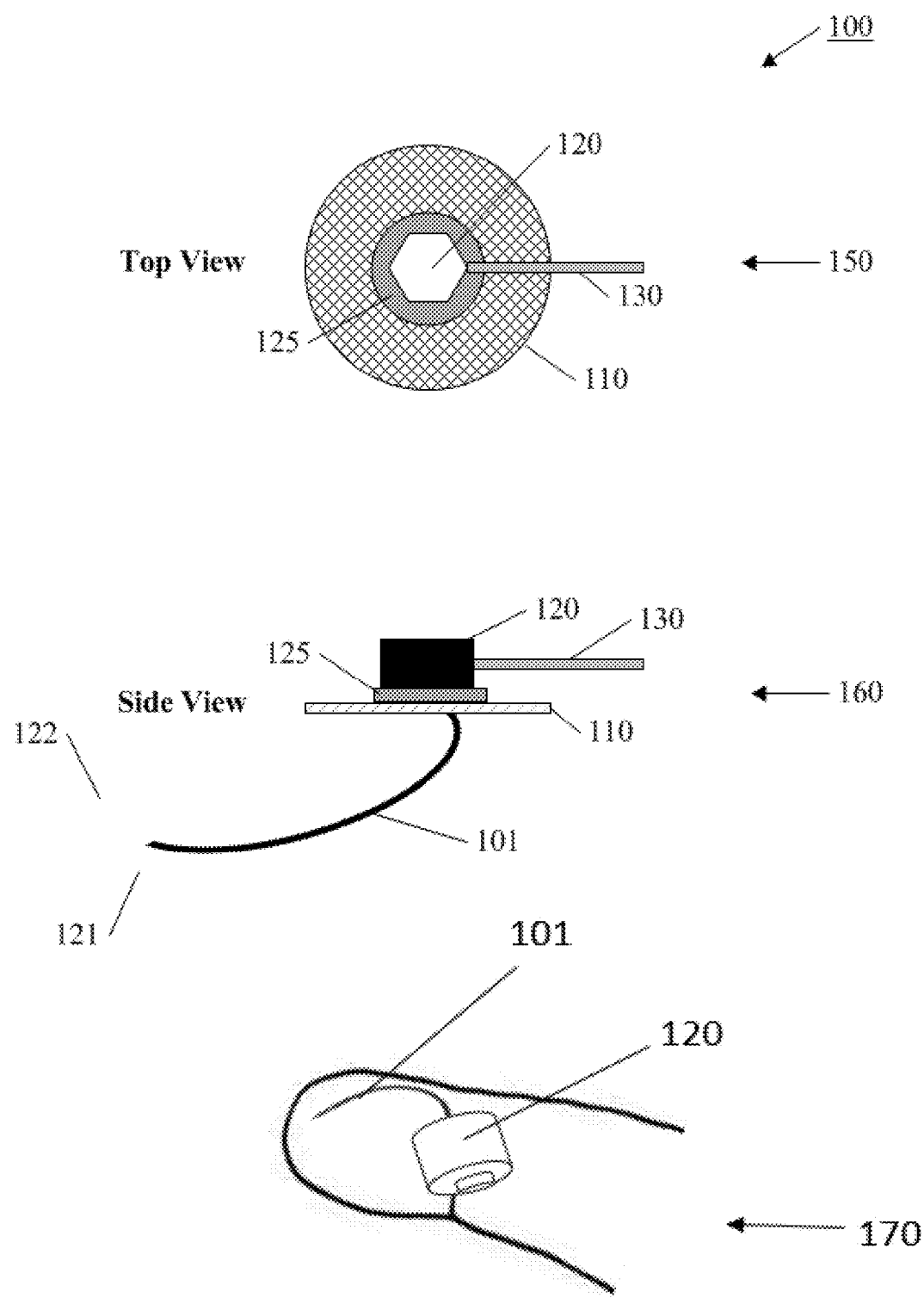
FIG. 1 has illustrations of a top view, a side view and a picture showing an extended use infusion set in accordance with the present invention.

While the invention will be described in conjunction with example embodiments, it will be understood that it is not intended to limit the invention to such embodiments. On the contrary, it is intended to cover all alternatives, modifications and equivalents as may be included within the spirit and scope of the invention.

DETAILED DESCRIPTION OF THE EXEMPLARY EMBODIMENTS

The embodiments and examples shown here are to provide enough information to fully understand the invention.

One skilled in the art will understand how minor changes or deviations can be made and still be within the scope of the invention. The following description of exemplary embodiments of the invention is not intended to limit the scope of the invention to these exemplary embodiments, but rather to enable any person skilled in the art to make and use the invention. To assist in a clear and unambiguous understanding of the disclosure, the following definitions are used:

Definitions

- A bolus is generally a single dose of insulin, typically a larger dose administered at once and often at mealtime. The purpose is to provide additional insulin to help the body address the carbohydrate intake of the meal. A bolus may also be given if there are other foreseen or unforeseen events affecting blood sugar. A bolus may be administered via an infusion set which also delivers basal insulin, or may be injected separately.
- The basal insulin level is the amount of insulin referred to as necessary to address the diabetic patient's need for insulin between meals or other foreseen or unforeseen events, such as mealtime or snacks. The basal insulin dosage is often a lower level, delivered more regularly or nearly continuously, between meals.
- A cannula is similar to a hollow metal needle, but often made of a softer, flexible material which can bend. Some cannula designs incorporate an introducer needle, which may or may not be hollow, to help the cannula achieve its desired position.
- An introducer needle is a hollow or solid needle which generally does not deliver medicine itself, but instead helps the cannula penetrate the skin and achieve its desired position to deliver medicine for therapeutic benefit at a subdermal or subcutaneous depth and position.
- A needle is a sharp object which is used to penetrate the skin and push through the body to a desired depth or position. A needle may be hollow or solid. It may allow medicine to travel through it into the body, or it may act only as an introducer needle for a softer and/or more flexible cannula and be retracted after its positioning function, or it may perform both medicine delivery and introducer functions.
- A depot is a location where medicine is delivered by the needle or cannula, and generally the "depth and location" within the patient tissue where the medicine is absorbed by the body.
- A kink is a bend in the cannula that results in a deformation to the cross-section at a point. This deformation may be inelastic, meaning that the original circular (or other) cross sectional shape may not fully restored upon removal of the original stress, and that the material may be permanently weakened at the site. A kink is typically a point at which a previous cross section is deformed to an edge or corner on approximately opposite sides of the cross section. This deformation to the cross-section can result in a reduction of flow at the kink, and in some cases, near full obstruction. Furthermore, once a kink has occurred at a site in the cannula, usually less stress is required to trigger a kink at the same site subsequently, even if the previous kinks at the site have been nearly fully removed. The other primary characteristic of a kink is a bend along the longitudinal axis of the cannula beyond its minimum bend radius.
- Kinkless describes a cannula that is not expected to undergo deformation to the point that would be described as a kink (reduction in cross-sectional area, with inelastic deformations resulting in a reduced cross section which is no longer fully circular, or an elastic deformation of the original cross-section, but instead may be characterized by one or more corners in the cross-section, often at opposite sides). Any deformation is within the elastic range, meaning that upon removal of the stress, the original cross-sectional shape is fully restored. The area is not weakened to the point that subsequent lower stresses at the same location result in a kink. The kinkless cannula also does not undergo a bend along its longitudinal axis beyond its minimum bend radius.

Embodiments of the present invention are directed to a medical infusion set constructed to insert a flexible cannula to an initial therapeutic depth and position under the skin of a patient. Herein, the term "depot" may be used to identify a particular depth and position for a subdermal or subcutaneous insertion of a cannula. At a later time after, such as 24 hours after the initial insertion, or when the initial insertion has a measured degraded therapeutic effect, the insertion set is capable of repositioning the cannula to a new therapeutic depth or position. In this way, therapeutic effect may be greatly increased at the new depth and position site, enabling an extended use of the insertion set.

A particular embodiment is directed to an infusion set with the capability to have an initial insertion to a therapeutic depth and position of a curved needle, which may thereafter be further inserted or partially removed for the purposes of achieving a new depot.

A preferred embodiment is directed to an infusion set with the capability to have an initial insertion to an effective depth and position of a sensor such as for a continuous glucose monitor (CGM), which may thereafter be further inserted or partially removed for the purposes of achieving a new depth and/or position at which interaction with biological processes can provide useful data.

A preferred embodiment is directed to an infusion set with the capability to have an insertion to an effective depth and position of a sensor such as for a continuous glucose monitor (CGM) for the purposes of interaction with biological processes that can provide useful data.

In another aspect of the invention, preferred embodiments are directed to providing a substantially kink free insertion of the infusion set. Although the kink free embodiments are specifically identified in FIGS. 11 to 14, it will be understood that the embodiments disclosed in FIGS. 1 to 10 may also advantageously provide for substantially kink free insertions. In a similar manner, the embodiments identified in FIGS. 11 to 14, although specifically directed toward the kinkless aspect, may also advantageously be constructed to have an initial therapeutic setting location, and then be resettable to a second therapeutic position, as more fully set out with reference to FIGS. 1 to 10.

As shown in the included figures, the illustrations depict instances of infusion sets inserted into the skin for the purposes of delivering fluid medicine into the tissue beneath the outer layer of skin, such as insulin for the treatment of diabetes subcutaneously. However, it will be understood that the invention may also be utilized for delivery of other medicine, hormones, vitamins, saline, including fluids containing dissolved or suspended solids if in the future such a treatment is created. The invention may be used for the placement of sensors capable of measuring biological information, such as glucose levels, ketone levels, lactate levels, salinity, red or white blood cells, T-cell counts, dissolved oxygen, or the like on a continuous or intermittent basis, whether for information, entertainment, or compliance purposes only, as part of a feedback loop in medicine delivery, or to aid in a combination of manual and automated administration of fluid described above, whether that manual administration is through the infusion set or administered elsewhere on the body.

Referring now to FIG. 1 an infusion set 100 is illustrated. Infusion set 100 is illustrated in a top view 150 as well as a side view 160. Infusion set 100 is designed and intended to insert a curved cannula 101 subcutaneously into a human to enable a medicine or therapeutic to be delivered into the patient at a desirable depth and position. As illustrated, the infusion set 100 has already been inserted under the patient's skin to an initial depth and position. It will be understood that a housing, mechanism, or introducer needle may have been used to insert and set the infusion set 100 into the illustrated position. Example insertion mechanisms are illustrated in following sections.

The infusion set 100 is attached and secured to the human body using an adhesive pad 110. A head piece 120 connects tubing 130 to the source of the medication, which in some cases may be insulin driven from an infusion pump. Head piece 120 also connects to the cannula 101. Cannula 101 may be made from metal, plastics, or other materials appropriate for delivery of medication. It will be understood that the selection of material for cannula 101 may be particularly selected for the type of medication to be delivered. For example, some chemotherapy medications may degrade certain materials, so materials resistant to chemical damage would need to be selected. It will also be understood that the cannula 101 may use an introducer needle to initially place the cannula 101 to its desired position or location 121, with the introducer needle then being removed and discarded.

The headpiece 120 is used to insert the cannula 101 to and initial depth and position 121. Once inserted and properly adhered to the human body, the infusion pump can inject medication or therapeutic through tube 130 and into cannula 101, which delivers the medication at or near the initial depth and position 121. As is known, the therapeutic effect of the delivered medication will reduce over time, and typically the cannula would need to be removed and a new infusion set used. In many cases, the therapeutic effect remains quite high for the first 24 hours, and then begins to degrade over the next two or three days. Often, the infusion set would need to be changed after about 1 to 3 days, if not sooner.

To obtain an extended use, infusion set 100 has a reset mechanism 125 that can be used by the patient to extend the therapeutic effect using the same infusion set 100. In this way, infusion set 100 can have an extended life as compared to known infusion sets. A patient that is using an infusion set often has continuous or at least regular monitoring of therapeutic effect. In this way, the patient would become aware that the therapeutic effect of the medication has reduced over time, and the position of the cannula 101 needs to be changed. In other cases, the patient may begin to experience discomfort, and desire that the cannula be moved to a new depth or location. Accordingly, when the patient learns that therapeutic effect needs to be improved, or otherwise desires to move the cannula, the patient uses reset mechanism 125 to reset or reposition the cannula 101 to a new depth and position 122. In some cases, the new location may be at the same depth but a different position, in other cases only the depth will change, and in other cases both the depth and position can change.

It will be understood that reset mechanism 125 may be constructed to allow for only a single repositioning of cannula 101, or in some cases may be constructed to allow multiple repositioning. As will be understood, the decision on how many repositionings to allow may be made on a patient by patient basis, and can be influenced by the particular medication being infused, or the particular therapeutic effect that is desired. In another implementation, the repositioning may be initiated upon finding that glucose control is degrading or has become less effective. For example, a patient's mobile phone application may be in communication with his or her continuous glucose monitoring (CGM) device. The phone application will from time to time receive glucose and insulin data from the CGM device, and using algorithmic processes, may provide an alarm or notice to the patient that his or her glucose control is degrading. Upon receiving this notification, the patient may reset the position or depth of the cannula as discussed, resulting in improved glucose control. Using prior systems, the patient would be forced to make the decision either to accept the degraded performance for a longer period of time or to immediately endure the cost and pain of inserting a new infusion set at a new location.

Reset mechanism 125 may take several forms. For example, reset mechanism may take the form of a rotatable disk that upon rotation pushes the cannula 101 further into the patient, thereby moving the cannula from position 121 to position 122. It will be understood that the rotation may be done in a free-form manner, or may have hard stops that limit the possible change in insertion position and location. In another example, the reset mechanism 125 may be a snap receiver that allows the patient to press the head 120 into the reset mechanism 125 such that the cannula 101 is moved from position 120 to 122. In this way, the patient can simply press head 120 until it steps into a new, lower (closer to the skin) position in the reset mechanism 125. In another example, the reset mechanism 125 may be constructed to have a slidable track that would allow the user to reposition the head 120 latterly within the reset mechanism 125. Allowing the patient to latterly move the head 120 can reposition the cannula 101 from position 121 to position 122. The track may allow for free-form sliding, or may have stops or tabs for setting a more limited or precise positioning. It will also be understood that the tracks may be set to allow for one repositioning, or for multiple repositionings. It will be understood that many alternative mechanical structures can be used to reposition the cannula.

As described thus far, reset mechanism 125 is used to extend the cannula 101 either further or deeper into the patient, thereby repositioning the cannula into an area that has not yet received direct infusion of the medication. It will be appreciated that the reset mechanism 125 may also be constructed to retract the cannula 101, for example, by a few millimeters. In this regard, the head 120 may be rotated away from the reset mechanism to retract cannula 101; the head 120 may snap outward from the reset mechanism to allow the patient to pull the head 120 to a new position within the reset mechanism 125; or the head 122 may slide on a track that retracts the cannula 101. In this way, the cannula does not need to be constructed to reposition into new tissue but can be retracted into tissue that has already been pierced. It will be understood that many alternative mechanical structures can be used to reposition the cannula. Depending upon the specific construction of the cannula and reset mechanism, it may be possible to adjust only the depth, only the position, or both the position and depth.

Advantageously, the reset mechanism 125 enables the head 120 to be moved in a way that can reposition the cannula 101 to a new depth and position within the patient, thereby extending the time that the infusion set 100 may remain on the patient before replacement. Not only will this save discomfort and cost for the patient, but may also allow for a more consistent delivery of the therapeutic medication. For example, since the therapeutic value of the medication remains quite high for the first 24 hours, it may be possible to construct an infusion set 100 where the reset mechanism 125 allows for several small resets. In this way, the patient would be allowed, for example every 24 hours, to make a small repositioning of the cannula. In this way, the therapeutic effect of the medication can remain consistent and high. Although several mechanisms have been presented for the reset mechanism 125, it will be appreciated that there are several alternatives to providing a mechanical reset mechanism 125 for moving the position of cannula 101.

View 170 shows one example of the cannula 101 connected to the head 120. As can be seen, the needle 101 is curved, and constructed of a metal material. It will be understood that the cannula 101 can be constructed from several different materials, including combinations of materials (e.g., metal and plastic/polymeric), and may be made with different curves, lengths, and thicknesses. Advantageously, the cannula may be of a material choice (for stiffness, flexibility, hoop stress or other stress, torsional stability, etc.), or architecture (reinforcing internal or external structures, such as ribbing, microtubes, wall thickness, tip shape) to eliminate the need for an introducer needle for insertion or repositioning (hence "kinkless").

Figure 2:
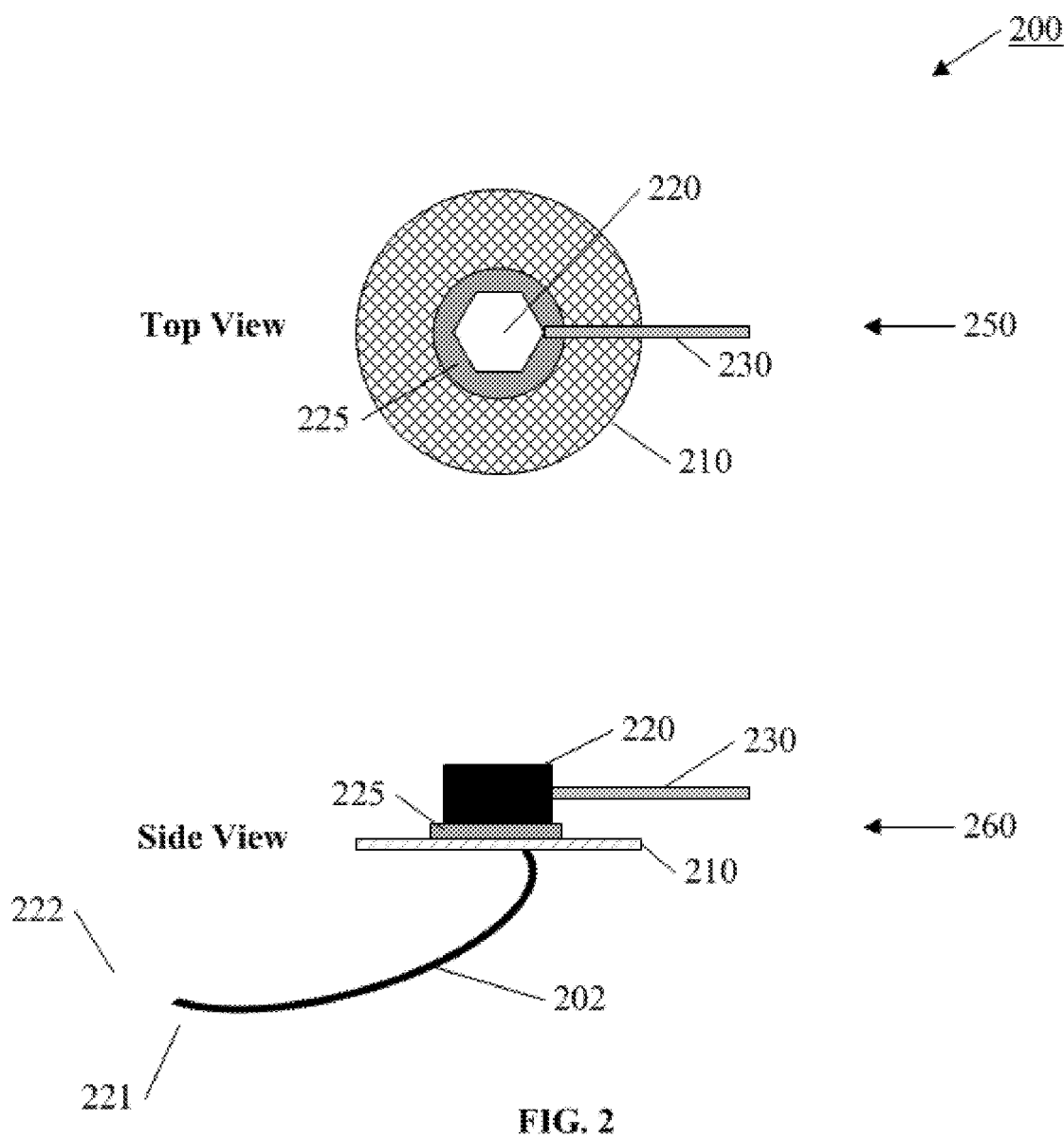
FIG. 2 has illustrations of a top view and a side view showing an extended use infusion set in accordance with the present invention.

FIG. 2 illustrates an infusion set 200 showing a top view 250 and a sideview 260. Infusion set 200 is similar to infusion set 100 described with reference to FIG. 1, so will only be briefly discussed to illustrate the differences. Infusion set 200 is also adhered to the human body with adhesive contact 210 and has a head 220 which allows medication to be injected through a tube 230. The medication flows from tube 230 into a curved needle 202. The head 220, and possibly an associated housing and insertion mechanism, positions the curved needle 202 to an initial depth and location 221. The curved needle 202 will often be made of a metal material, however stiff plastics or other materials may be used. The curved needle 202 has a sufficiently hard and sharp distal end and such that it can pierce and move through the patient tissue to properly position the needle 202. Infusion set 200 also has a reset mechanism 225 that can be used by the patient to set the curved needle from its initial position at 221 to a new position 222. In some cases, the new location may be at the same depth but a different position, in other cases only the depth will change, and in other cases both the depth and position can change. It will be understood that the reset position may take many forms, such as a rotatable disk, slidable on tracks, or a vertical snap mechanism as previously discussed with reference to FIG. 1.

Infusion set 200 does not need a disposable introducer needle, as the curved needle 202 acts both as the introducer needle, and as it is hollow, can itself act as the cannula for delivering the therapeutic medication. In this way, waste is reduced, and the curved needle 202 may be readily repositioned into new tissue. Advantageously, the infusion set 200 enables the curved needle 202 to be repositioned one or multiple times to extend the usable life of the insertion set 200.

Figure 3:
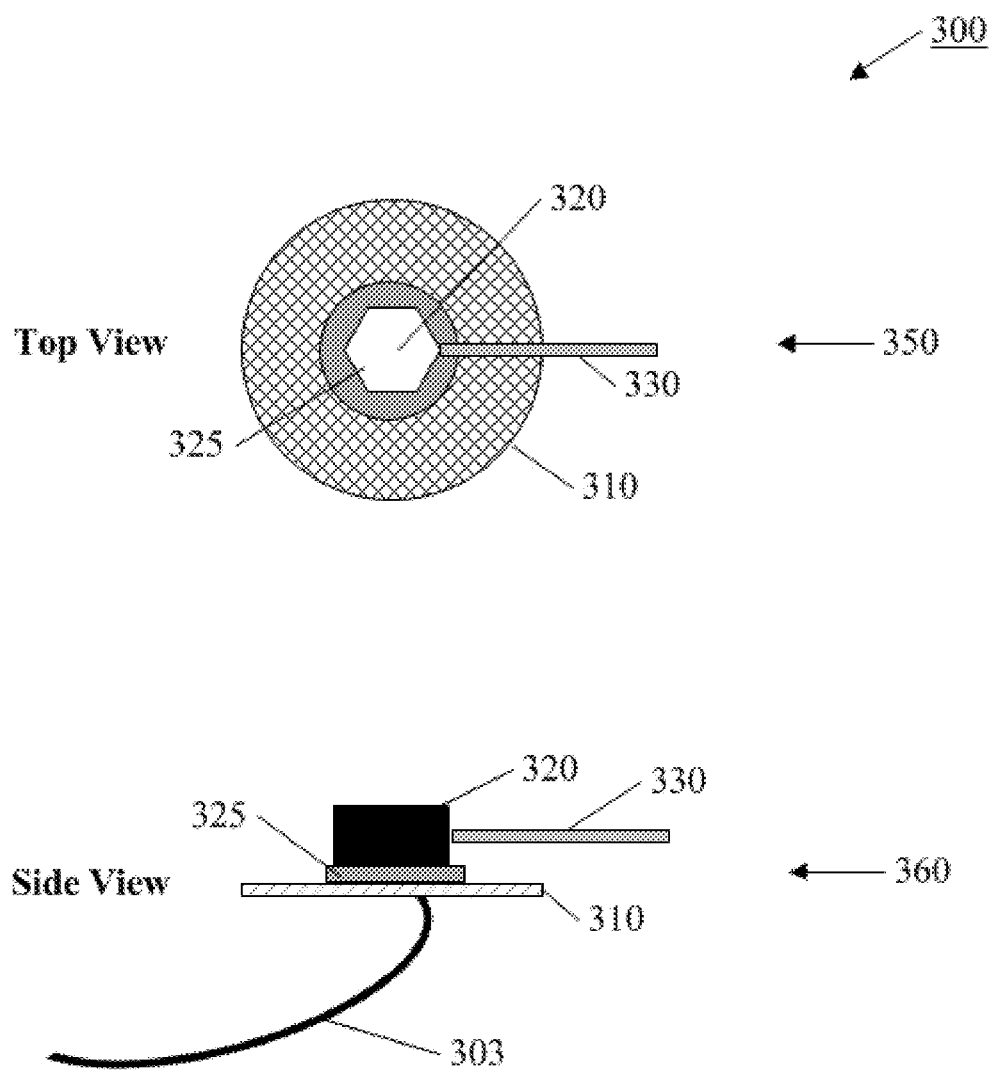
FIG. 3 has illustrations of a top view and a side view showing an extended use infusion set in accordance with the present invention.

Referring now to FIG. 3, a biological sensor 300 is illustrated with a top view 350 and a side view 360. The biological sensor 300 is positioned adjacent the skin of a human body and with the use of an inserted sensor 303 is able to detect certain types of biological activity within the body. For example, the inserted sensor may be constructed to detect the level of glucose in blood. In another example, the inserted sensor may detect other interstitial and/or blood components that may be indicative of the health and well-being of the patient. It will be understood that inserted sensor 303 may be constructed to detect a wide variety of conditions.

The biological sensor 300 is attached to the body with the adhesive pad 310, and has a head 320 that is used to assist in insertion of the inserted sensor 303. In some cases the head 320 may also contain electronics that cooperate with the inserted sensor 303 for detecting blood components. The inserted sensor 303 may have a tip that is sufficiently hard and sharp to penetrate the human flesh. In other cases, an introducer needle may be used to initially position the inserted sensor 303, and then the introducer needle is removed and discarded. Biological sensor 300 in some cases may also be constructed with the ability to inject the therapeutic medication. In such a case where the sensing and infusion functions are combined (not illustrated), a tube 330 may be connected to a medication source, such as an infusion pump, for delivering the medication. Further, the head 320 may be constructed to communicate to other medical devices, such as devices to present biological information, or to send control information an infusion pump. It will be understood that the communication may be done either wired or wirelessly.

The biological sensor 300 also has a reset mechanism 325. The reset mechanism 325 is similar to the reset mechanism 125 discussed with reference to FIG. 1. Accordingly, the reset mechanism 325 enables the patient to reposition the inserted sensor 303 to a new location, thereby enabling a longer usable life for the biological sensor 300 or allowing the sensor to maintain optimal performance and avoid biological response processes known to impact sensor duration and/or performance. In this way, costs and patient discomfort can be reduced, while also increasing the reliability and life for the biological sensor 300. It will be understood that the reset mechanism may be used to change only the depth, only the position, or in some cases change both the position and depth of the biological sensor.

Figure 4A:
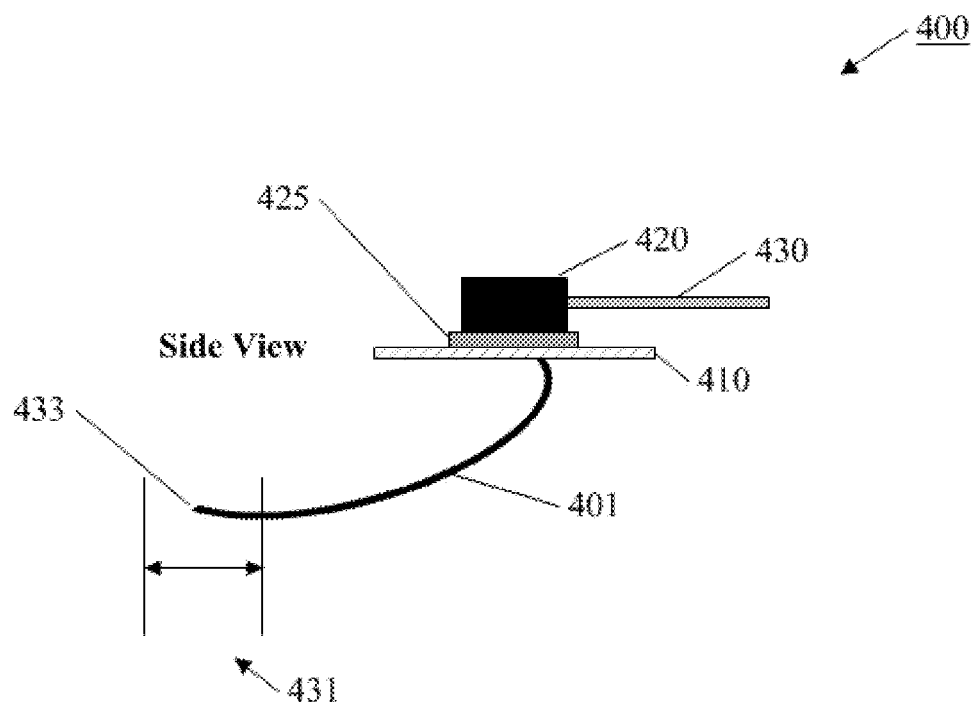
FIG. 4A has an illustration of a side view showing an extended use infusion set in accordance with the present invention.
Figure 4B:
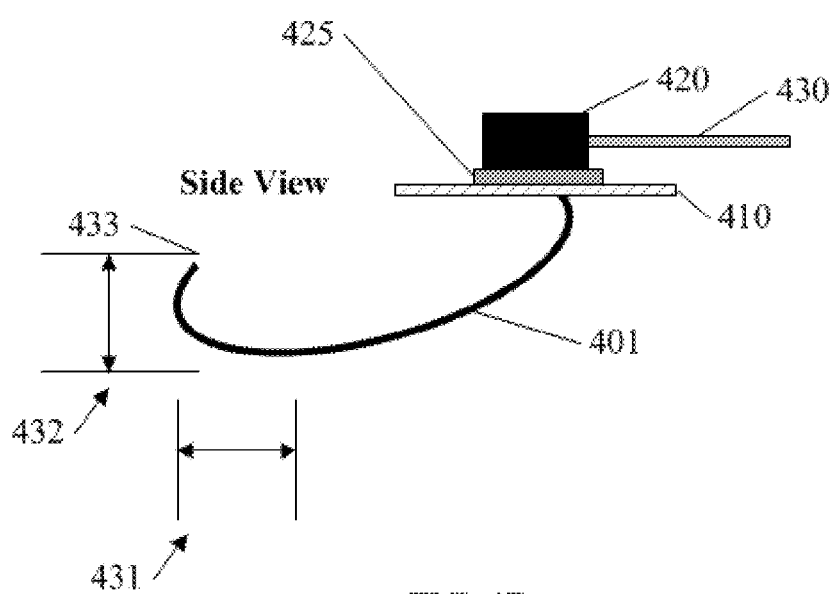
FIG. 4B has an illustration of a side view showing an extended use infusion set in accordance with the present invention.

Referring now to FIG. 4A and FIG. 4B, an insertion set 400 is illustrated. Insertion set 400 is similar to insertion set 100 described with reference to FIG. 1. Insertion set 400 has a needle 401 that connects to a head piece 420 that can receive medication through tube 430 for delivering a therapeutic medicine to a patient subcutaneously. The insertion set 400 is attached to the human body using an adhesive pad 410 in some cases, the head piece 420 and needle 401 will be inserted using a housing or disposable insertion mechanism or a reusable insertion mechanism to initially position the tip of the needle 433 to an initial depth and position.

Reset mechanism 425 is constructed to allow movement of the headpiece 420 in more than one axis. For example, the reset mechanism 425 may be set such that it may be rotated so that the needle 401 moves in a circular or oblong path changing both an X and Y position simultaneously, such as a helical coil like a spring. In another example, the reset mechanism for the 25 may provide for a screw rotation that allows the head 420 to both move in the Z axis as well as in the X or Y axis. Depending on the particular construction for reset mechanism 425, the reset mechanism 425 can be constructed to cause the repositioning of the tip of the needle 433 in one dimension, two dimensions 431 or in three dimensions as shown by 431 and 433. Or stated differently, the reset mechanism may be constructed to allow for a resetting of depth, a resetting of position, or a resetting of both depth and position.

In one particular example, the head 420 may rotate in the reset mechanism 425 so that the head 420 follows a sloped vertical guide that causes the head 420 to lift away from the skin or be pushed toward the skin depending upon the direction of rotation. At the same time, the needle 401 may be positioned off-center in the base of the head 420. In this way the same rotation motion within the reset mechanism causes the needle 401 to move in both the X and Y directions. In this way, the reset mechanism 425 causes a three-dimensional change in the position of the needle 401. In another example, the head 420 may be constructed to be rotatable and snapable to adjust its vertical position on an alignment track. At the same time, the head 420 may be positioned on a slidable track that allows the head 420 to be positioned in an X, Y, or Z direction. The ability to steer the head insertion allows the design to specifically locate the head location in the body and relative to desired biological components or structures (e.g., proximity to specific blood vessels or capillary beds, including the specific side or orientation relative to them such as above or below).

It will be appreciated that by enabling reset mechanism 425 to act in 2 or more dimensions, more flexibility in repositioning is obtained. In one advantage, an individual patient may find through experience that a change in a particular dimension is more comfortable for them, or gives a better and longer therapeutic result. In another advantage, a multidimensional repositioning can allow for positioning of more sophisticated needle or cannula shapes, such as helical or other three-dimensional shaped infusion devices.

Figure 5:
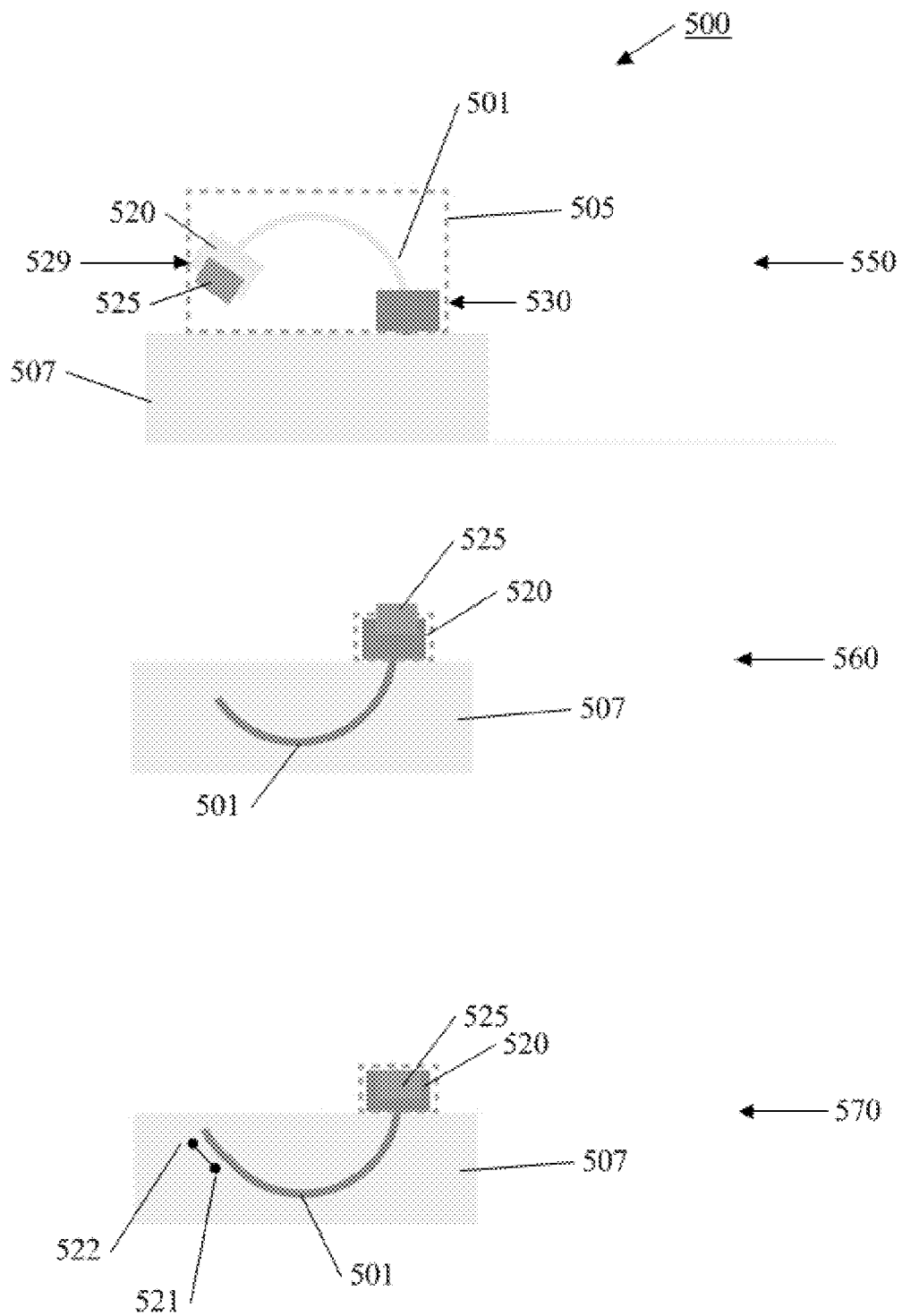
FIG. 5 has an illustration of a side view showing an extended use infusion set in operation and in accordance with the present invention.

Referring now to FIG. 5, a specific example of an infusion set 500 is illustrated. In view 550, the infusion set 500 is illustrated with the head 520 coupled to cannula 501 inside of infusion housing 505. Infusion housing 505 is temporarily provided to assist in the positioning of the cannula 501 under the skin. After insertion of the cannula 501, the housing 505 can be fully or partially removed. More particularly, the housing and insertion mechanism is intended to move the head 520 from an initial position 529 to the final position 530. In this way, the cannula 501 pierces the skin 507 and enables the cannula 501 to be positioned at a therapeutic depth and position in the patient tissue 507.

View 560 shows the infusion set 500 with the cannula 501 positioned at its initial depth and location 521. The head 520 is positioned up against the patient skin, and is adhered to the skin using an adhesive pad 510. At this point, the infusion set 500 may be used from 1 to 7 plus days while maintaining sufficient therapeutic effect from the medication. It will be understood that the length of time it may be used will vary depending upon patient, medication used, and desired minimum effect. Reset mechanism 525 is also in its initial position, and has not yet been activated.

View 570 shows infusion set 500 after the reset mechanism 25 has been activated. Here, the reset mechanism is illustrated as a snap button that the patient presses further into head 520. Although a single step location is illustrated, it will be understood that several intermediate steps may be provided, thereby allowing for multiple resettings for depths, positions, or positions and depths. It will also be understood that the reset mechanism 525 may be in the form of a rotatable disk that is inserted through a screw-like mechanism. Once the reset mechanism 525 has been activated, the cannula 501 is moved from its initial depth and position 521 to a new repositioned depth and location 522. In this way, the therapeutic effect for the medication is improved or maintained. Although the reset mechanism 525 is illustrated as moving the cannula 501 further into the body, it will be understood that the reset mechanism 525 can be constructed such that the reset mechanism retracts the cannula 501 (e.g., a few millimeters). In this way, the cannula 501 would not need to be constructed to pierce or penetrate new tissue, but retracts into the initial existing wound site. For the instance in which the cannula will be repositioned in such a way that it will need to pierce or penetrate new tissue, its material selection and architecture may be chosen so as to permit repositioning without an inserter needle and without kinking ("kinkless" cannula). It will also be understood that the infusion set can easily be modified to insert and reset a biological sensor, such as a sensor for glucose monitoring.

Figure 6:
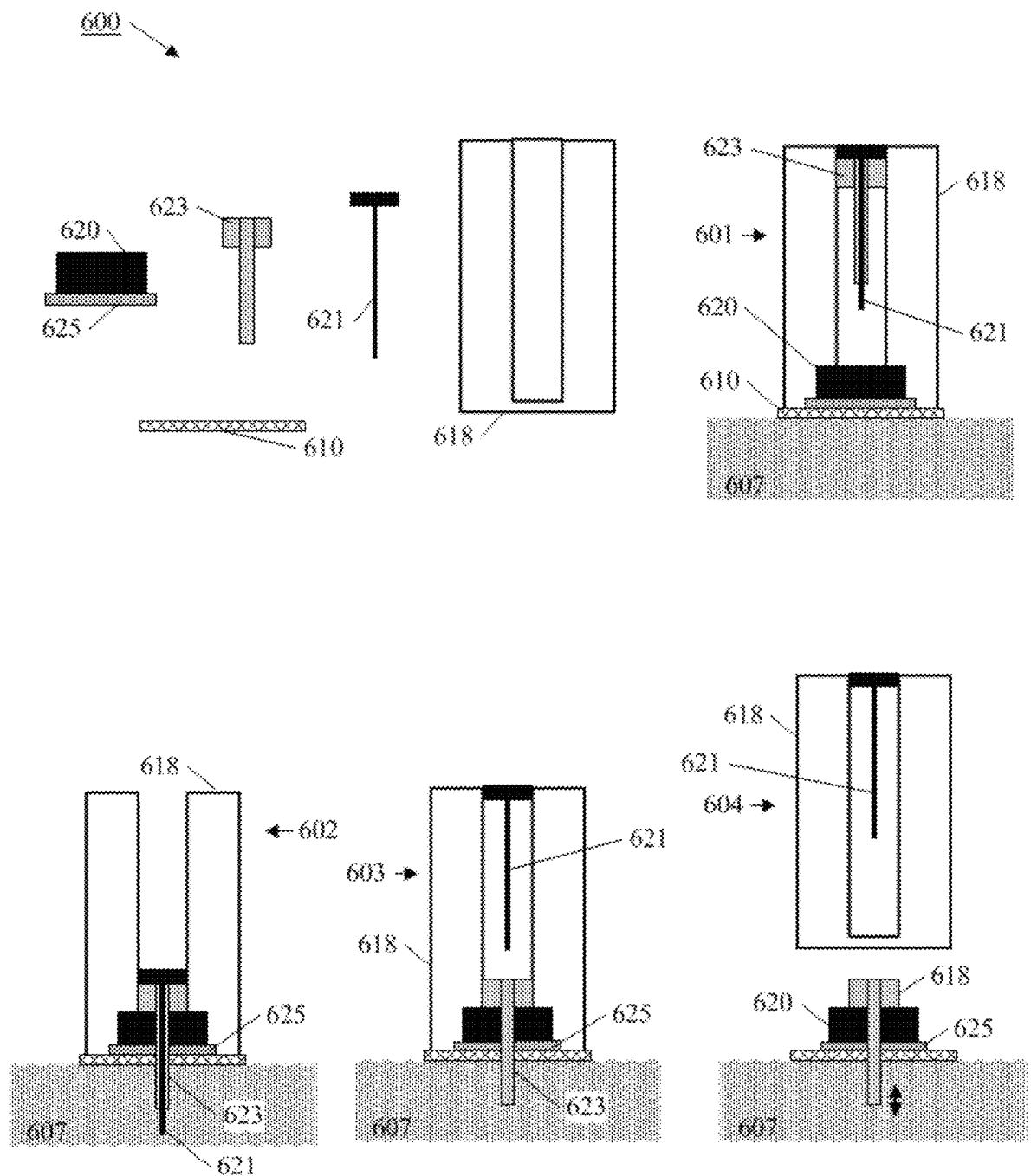
FIG. 6 has illustrations of a partial cut-away front view showing an extended use infusion set in operation and in accordance with the present invention.

Referring now to FIG. 6, another infusion set 600 is illustrated. In view 601, infusion set 600 is illustrated prior to insertion and use. In this position, a housing 618 is used to assist with the insertion and initial placement, and after the initial insertion and placement, the housing 618 is discarded or set aside for later reuse, within sanitary guidelines. The housing 618 assists in adhering the infusion set 600 to the skin 607 using adhesive pad 610. The housing contains an introducer needle 621 in and providing a path for the cannula 623 to be positioned at its initial depth and location. The infusion set 600 also has a head piece 620 that cooperates with a reset mechanism 625 to provide for repositioning of the cannula 623 at a later time. It will be understood that the setting mechanism and cannula can be constructed and made to cooperate in a way that can change only the depth, change only the position, or change both the depth and position.

View 602 shows the housing 618 with the introducer needle 621 fully extended in two the patient's tissue 607. In this position, the cannula 623 is also positioned in to its initial depth and location. View 603 shows that the introducer needle 621 has been removed from the patient, while the cannula 623 remains in its initial position. It will be understood that removal of the introducer needle may be accomplished in several ways. For example the introduced needle may be removed as part of a manual motion by the patient to remove the insertion mechanism and housing. It will be appreciated that the introducer needle can be removed concurrent with removal of the housing or may be done prior to removing the housing. In one application, the introducer needle is removed by a spring or other tension device prior to removal of the housing. In this way, the removal of the introducer needle from the patient is independent of the action to remove the insertion mechanism and housing.

View 604 shows that the housing 618 and introducer needle 621 are removed and discarded or set aside for later reuse, within sanitary guidelines. The cannula 623, head 620, and reset mechanism 625 remain attached to the patients's skin. At a later time after the therapeutic effect of the medication has been reduced, then the patient can use the reset mechanism 625 to reset the depth or location of the cannula 623 as previously discussed. It will also be understood that the infusion set can easily be modified to insert and reset a biological sensor, such as a sensor for glucose monitoring.

Figure 7:
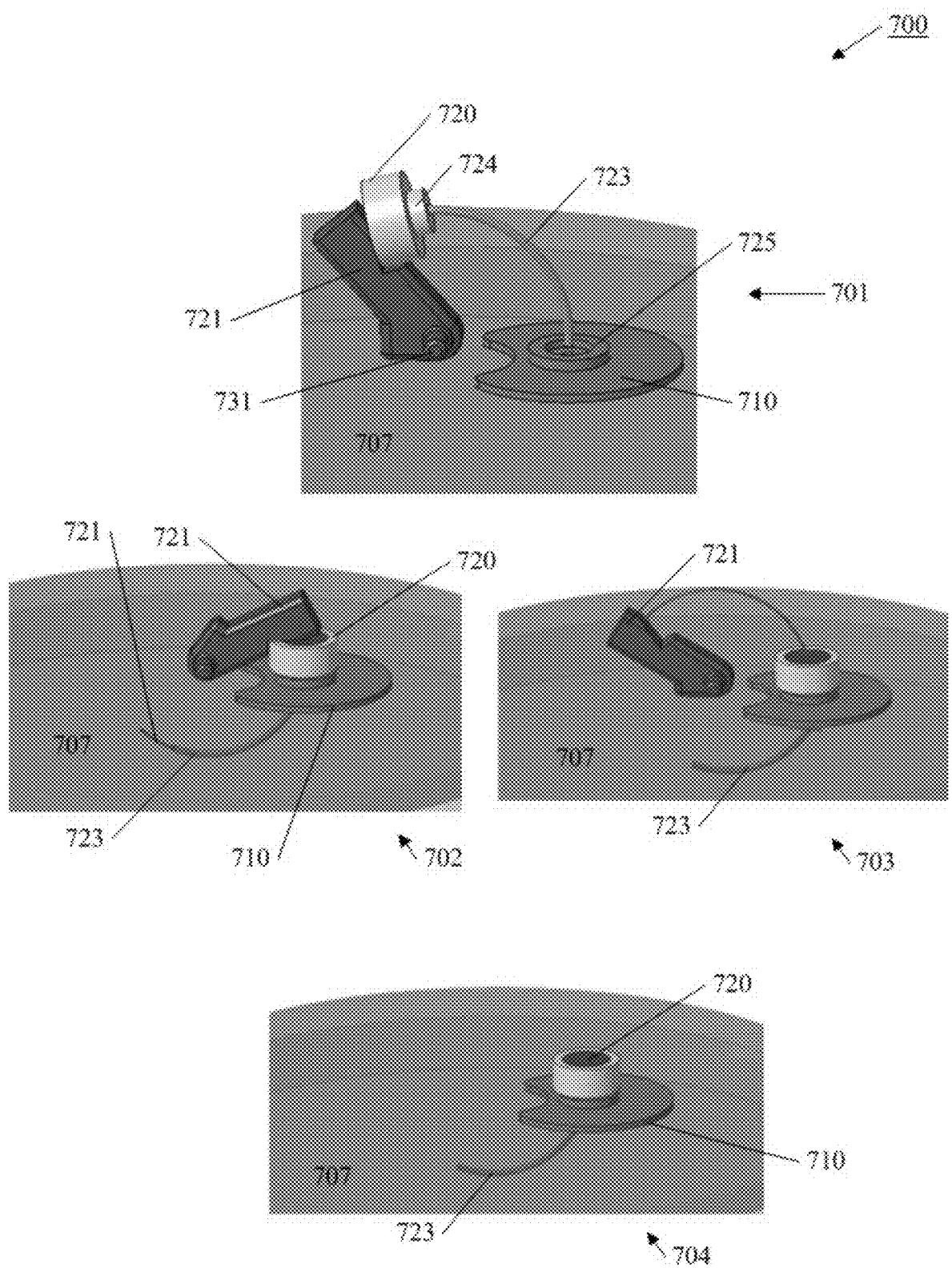
FIG. 7 has illustrations of a partial 3-D view showing an extended use infusion set in operation and in accordance with the present invention.

Referring now to FIG. 7, an infusion set 700 is illustrated. Infusion set 700 is constructed to require the use of an introducer needle 721 to first pierce the patient's skin and then position the cannula 723 into the tissue at its initial depth and location. The introducer needle 721 is illustrated as a two-part device. First, the introducer needle has a large insertion tab that is hinged 731 and connected to a housing (not illustrated). The needle portion of the introducer needle 721 is positioned inside of cannula 723, and constructed so that it extends from the distal end of cannula 723. Typically, the introducer needle will be constructed to extend approximately 3 mm from the end of cannula 723, although it will be appreciated that other distances may be used. As the needle tab 721 is rotated around hinge 731, the needle 721 is inserted into and through the human tissue, and also the head 720 is moved toward the adhesive base 710.

View 702 shows the introducer needle 721 fully rotated towards the insertion point. In this way, the head 720 has been moved to the adhesive base 710, and the introducer needle 721 has fully penetrated the patient tissue, thereby enabling cannula 723 to be put in its initial depth and location. View 703 shows the introducer needle 721 retracted. Upon retraction, the introducer needle may be discarded, while the hinge mechanism and housing may be discarded or set aside for later reuse, within sanitary guidelines. In this way, the head 720 remains attached to the adhesive base 710 and the cannula 723 is at its initial depth and location, as illustrated in view 704. The insertion set 700 may now be connected to a medication source, such as an infusion pump, and medication effectively delivered to the initial tissue position and location.

The insertion set 700 has a reset mechanism 725 for repositioning cannula 723 after initial insertion. In operation, the reset mechanism 725 cooperates with a portion 724 of the head 722 effectuate the repositioning. For example, the portion 724 may be threadably adjustable within the reset mechanism 725. In this way, a patient, when therapeutic effect needs to be improved, can rotate the head 722 to move the cannula 723 further into the tissue, or alternatively to retract the cannula 723. In another example, the portion 724 may be constructed to snap at a second location into reset mechanism 725. In this way, when therapeutic effect needs to be increased, the patient simply presses the head 720 in a downward fashion, thereby causing the portion 724 to step into a new location into reset mechanism 725. This action would cause the cannula 723 to move to a new depth and position. In an alternate example, the patient may be able to lift the portion 724 away from the reset mechanism 725, thereby extracting the cannula 723 a few millimeters into a new position. It will be understood that the setting mechanism and cannula can be constructed and made to cooperate in a way that can change only the depth, change only the position, or change both the depth and position. It will also be understood that the infusion set can easily be modified to insert and reset a biological sensor, such as a sensor for glucose monitoring.

Figure 8:
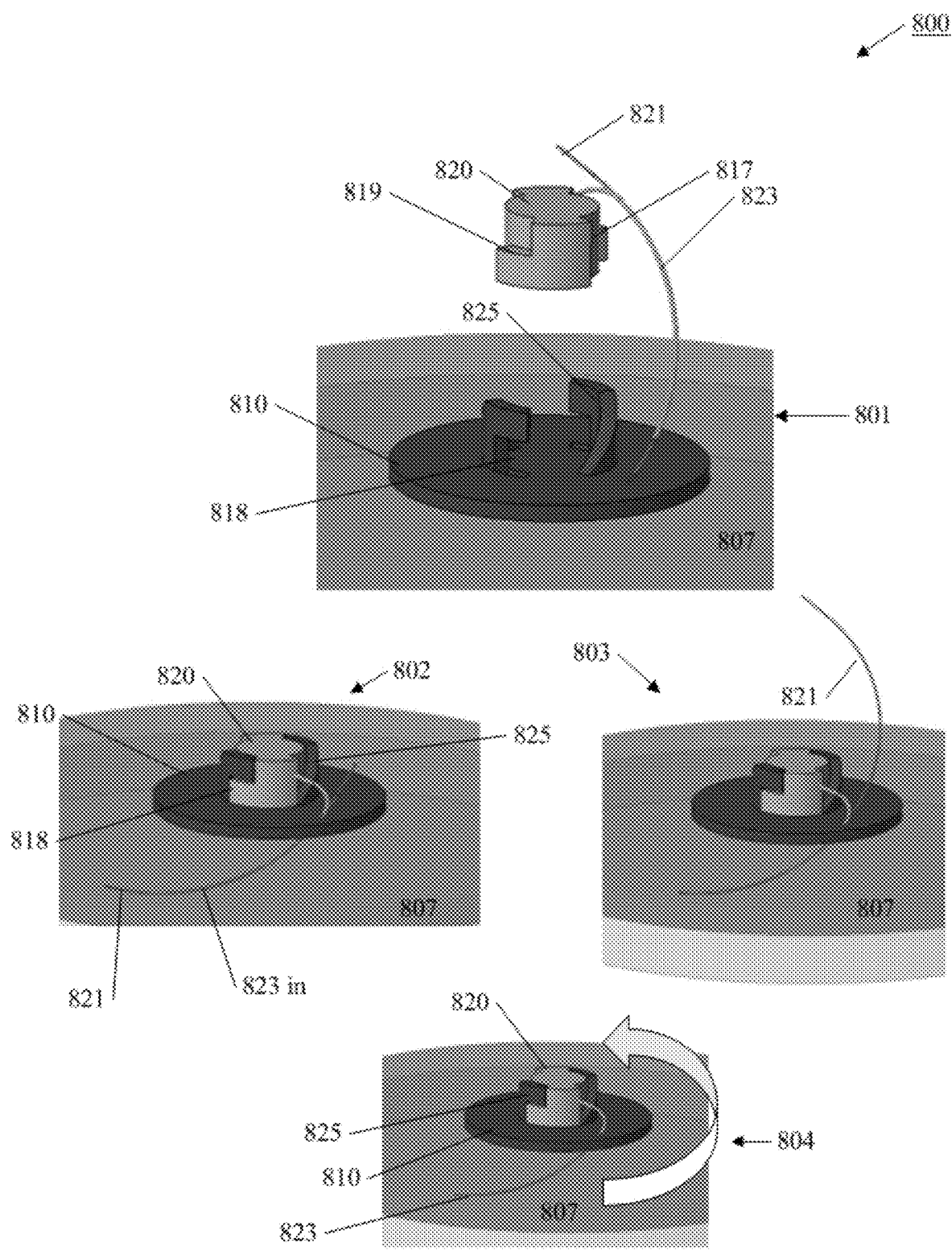
FIG. 8 has illustrations of a partial 3-D view showing an extended use infusion set in operation and in accordance with the present invention.

Referring now to FIG. 8, an infusion set 800 is illustrated. Infusion set 800 has an adhesive base 810 that secures against the skin of a patient 807. Infusion set 800 uses an insertion housing and mechanism (not shown) to position a cannula 823 at an initial depth and location. As illustrated, insertion set 800 uses an introducer needle to assist in initial positioning of cannula 820. As illustrated in view 801, a head piece 820 is mechanically moved by the housing into the adhesive base 810. In this way, the introducer needle 821 pierces and penetrates the tissue of the patient, and is used to position cannula 823 to its initial position and depth. In particular, the head piece 820 has a sloped portion 817 but cooperates with a sloped portion on the reset mechanism 825 to enable the headpiece 820 to be rotatably received into the reset mechanism 825. Rotation is complete when the tab portion of the head 820 is received into the tab portion 818 of the reset mechanism 825. As illustrated in view 802, the head portion 820 is fully rotated and received into the reset portion 825. In this way the tab 819 is fully received into the receiver tab 818. In this position, the introducer needle is extended fully into the patient tissue, and the cannula 823 is positioned at its initial depth and location.

As illustrated in view 803, the housing and any insertion mechanism may be removed, which also removes the introducer needle, all of which may be discarded. In this way, the head 820 remains in the reset mechanism 825. As illustrated in view 804, at a later time, when the patient desires to reset the cannula 823, the head 820 may be rotated within the reset mechanism 825 to retract cannula 823, thereby setting it into a new therapeutic position. In another example (not illustrated) the headpiece may initially be positioned not fully inserted into the reset mechanism, and then rotation of the headpiece by the patient can cause a further insertion of the cannula 823. In this latter case, the cannula tip would need to be hard enough or sharp enough to allow for a further insertion through patient tissue. The kinkless cannula design, in material and/or construction shall have adequate structural integrity for the repositioning.

It will be understood that removal of the introducer needle may be accomplished in several ways. For example, as described above, the introduced needle may be removed as part of a manual motion by the patient to remove the insertion mechanism and housing. It will be appreciated that the introducer needle can be removed concurrent with removal of the housing or may be done prior to removing the housing. In one application, the introducer needle is removed by a spring or other tension device prior to removal of the housing. In this way, the removal of the introducer needle from the patient is independent of the action to remove the insertion mechanism and housing.

It will be understood that the setting mechanism and cannula of FIG. 8 can be constructed and made to cooperate in a way that can change only the depth, change only the position, or change both the depth and position. It will also be understood that the infusion set can easily be modified to insert and reset a biological sensor, such as a sensor for glucose monitoring.

Figure 9A:
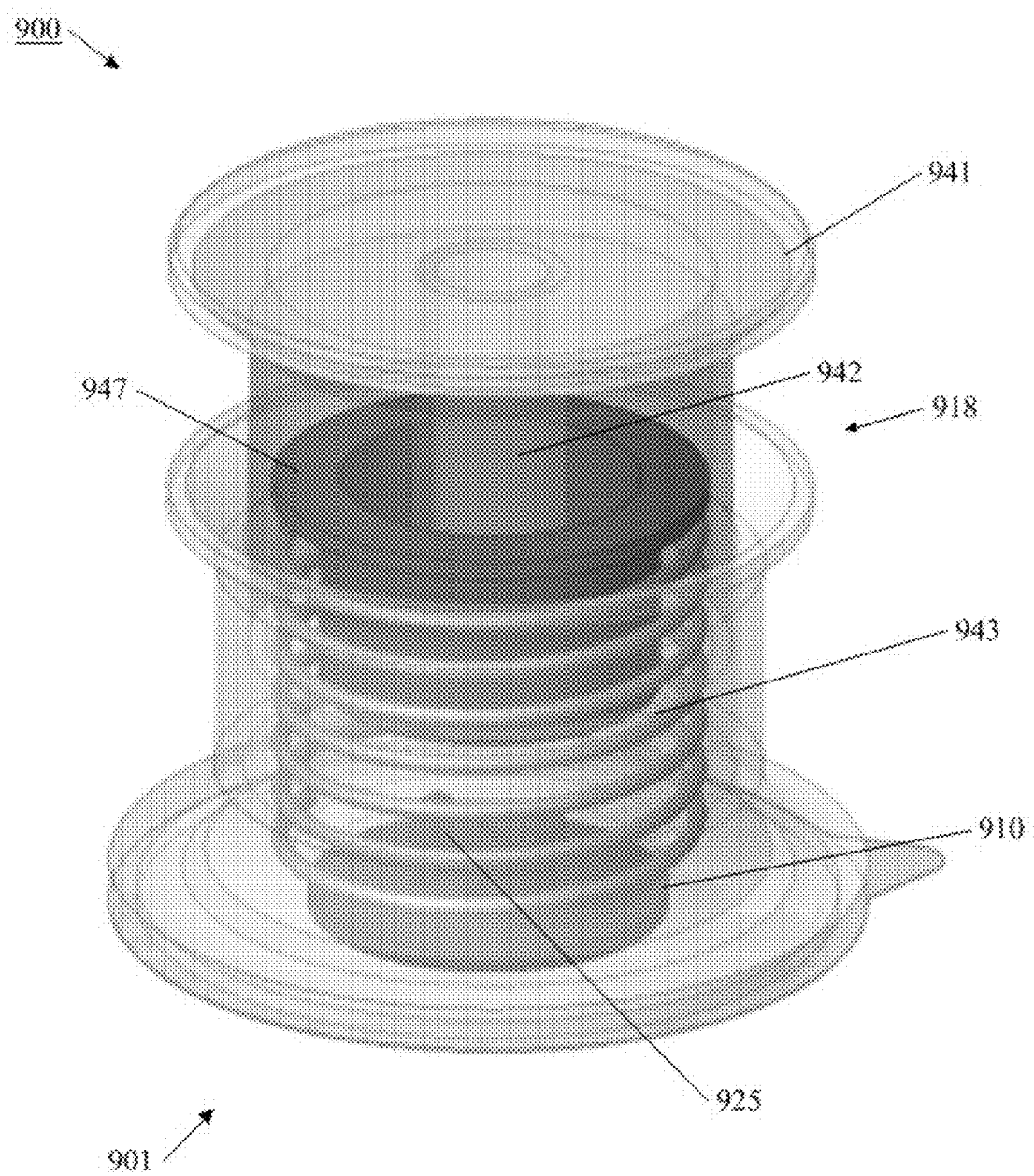
FIGS. 9A, 9B and 9C are partial 3-D views of an extended use infusion set in operation and in accordance with the present invention.
Figure 9B:
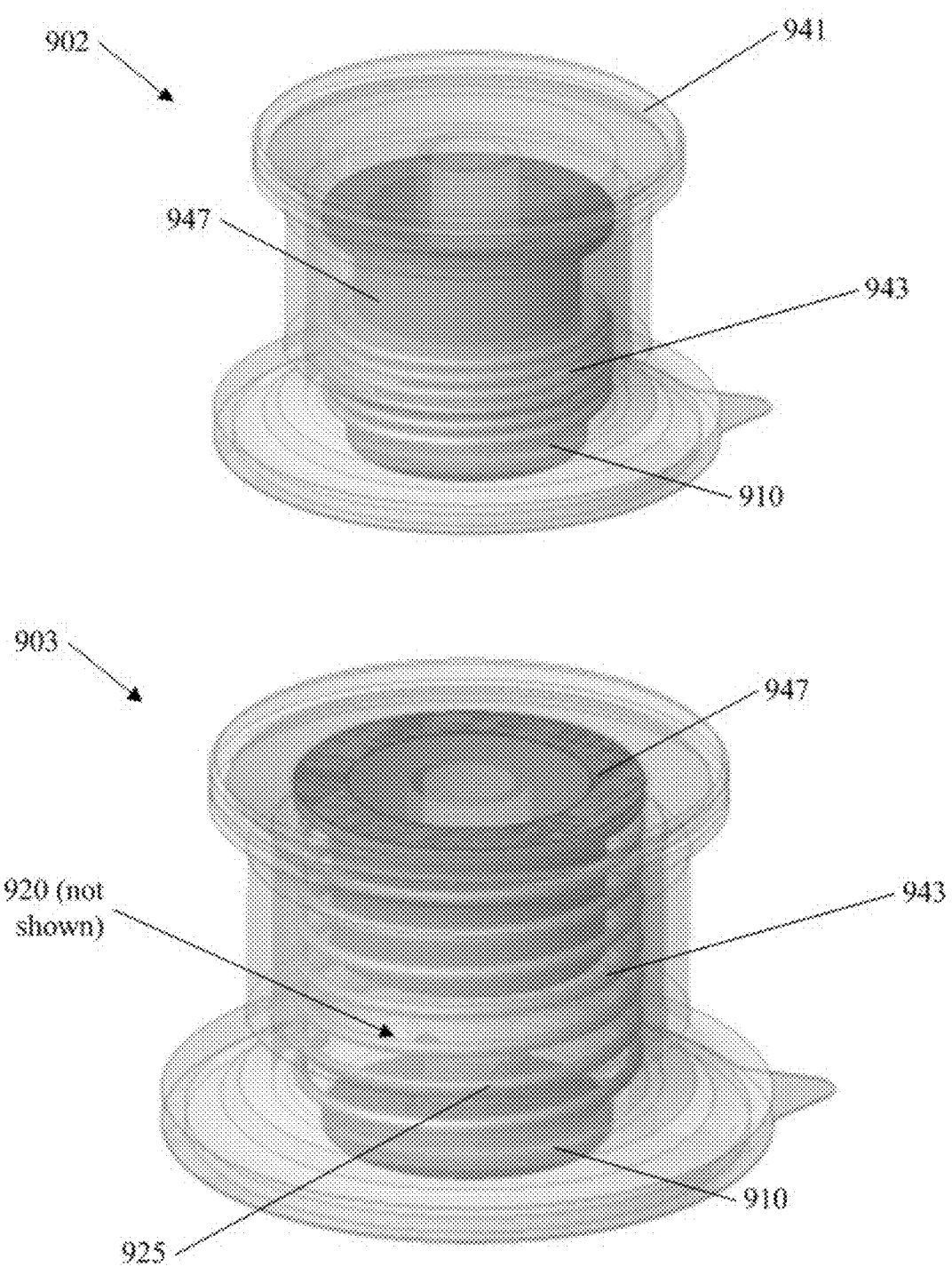
Figure 9C:
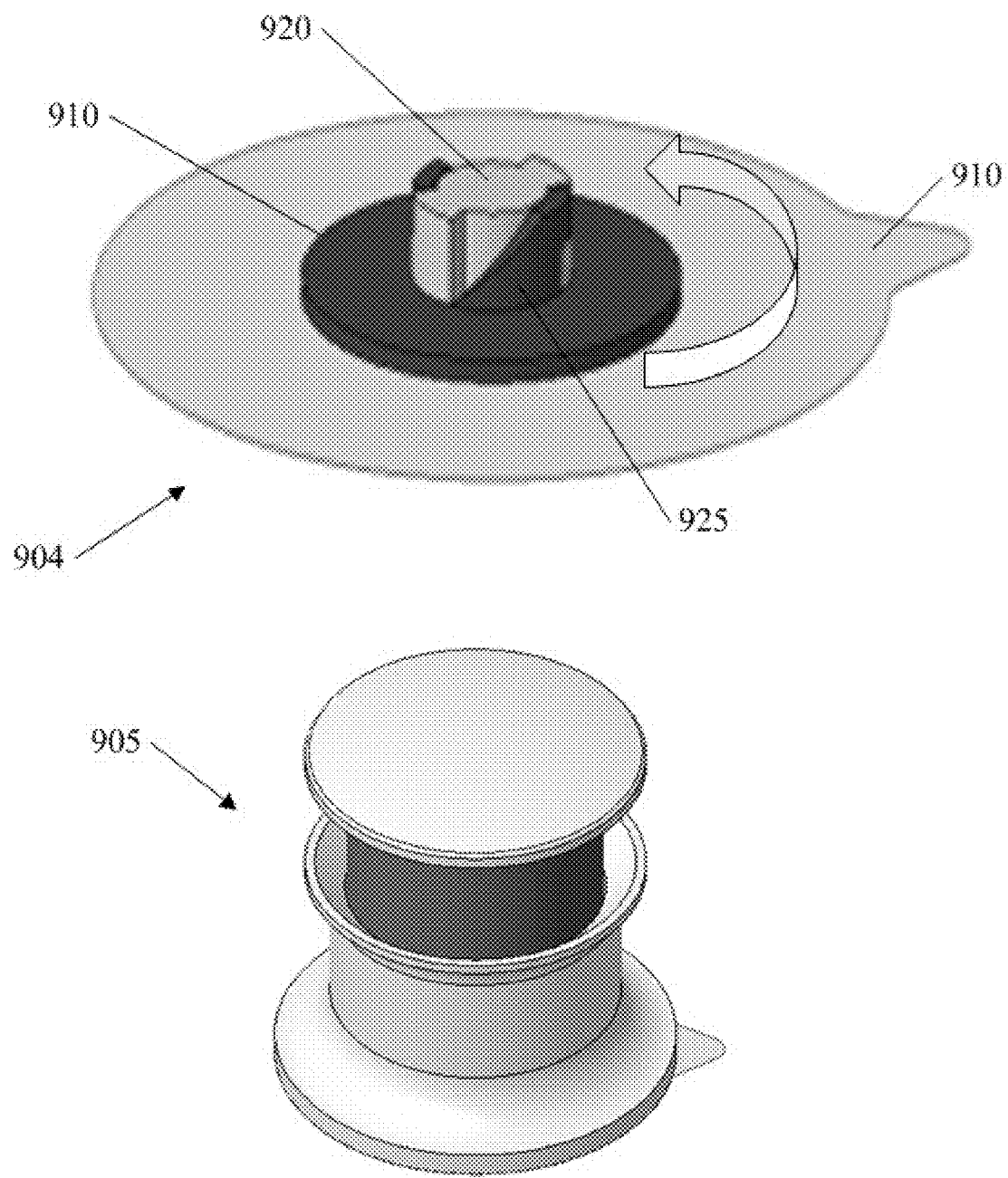

Referring now to FIGS. 9A, 9B and 9C, an infusion set 900 is illustrated. Infusion set 900 is one specific example of a housing and insertion mechanism that may be used to insert and initially position the infusion set 800 illustrated with respect to FIG. 8. It will be understood that there are a wide variety of insertion mechanisms and housings that may be used. Insertion set 900 has a housing 918 that has a tube piece 942 that initially holds the head piece 920. As illustrated in view 901, the headpiece 920 is retained securely in the tube 942 and is spaced away from the reset mechanism 925. In particular, the insertion mechanism 900 has a plunger 941 that is used by the patient to press the tube 942 through a sleeve 947 to move the head 920 toward the reset mechanism 925. As illustrated, a spring 943 is used to provide a force that initially keeps the plunger 941 fully extended away from the body of the patient. The housing 918 also has an adhesive pad which may be used to secure the infusion set 900 to the patient of the body.

View 902 shows that the patient has moved the plunger 941 fully towards the adhesive pad 910. As the patient moves plunger 941 such that the tube 943 moves downward in sleeve 947, the head 920 begins to engage the reset mechanism 925. Due to the curved and sloped nature of reset mechanism 925, the downward motion of the plunger 941 causes the head 920 to rotate clockwise and continue in a rotating downward motion until its tab locks into a mating tab of the reset mechanism 925, as described with reference to FIG. 8. It will be understood that the rotation direction can be set according the system requirements, for example, in some cases it may be useful to allow for a counterclockwise rotation to move the cannula downward. When the plunger 941 has been fully depressed by the patient, and the head 920 is firmly positioned in the reset mechanism 925, the patient may release the plunger 941, causing the spring 943 to expand, as illustrated in view 903. Alternatively, the spring maybe compressed to an actuation point which automatically engages the spring removal mechanism to retract the introducer needle from the body. As the spring expands, the introducer needle could then further be removed or even lockingly captured in the insertion mechanism. Further yet, expansion of the spring and removal of the insertion needle may cause the attachment between the insertion device and the housing base to be detached or decoupled, allowing for easy removal of the insertion device from the body and infusion site. For purposes of ease of illustration, the headpiece 920 is not shown in view 903. However, at this point the headpiece 920 would be firmly secured into the reset mechanism 925. The patient can now remove the housing 918 with all its associated setting mechanisms, including any introducer needle, which can be discarded. Advantageously, a flexible, yet sufficiently rigid cannula with enough structural integrity to not kink during insertion without an introducer needle and thereafter in use, and even during one or more repositionings may also be utilized.

As illustrated in view 904, with the housing removed, the head 920 remains securely attached into the reset mechanism 925, which is attached to the adhesive pad 910. The patient may now connect an infusion pump or other medicine insertion device to the head 920, and begin infusing medication into their body at the initial insertion depth and position. As previously described, the patient should obtain full therapeutic effect for a period of time, of at least 24 hours. At a later time, when therapeutic effect has been reduced at the initial site, the patient may reset the position of the cannula to obtain a new depth and location, thereby increasing therapeutic effect. As illustrated, the patient may rotate the head 920 in a counterclockwise direction to retract the cannula a few millimeters from the body. This places the cannula in a new therapeutic location, which will enable an extended and advantageous therapeutic effect for the medication. As described with reference to FIG. 8, the reset mechanism 925 may allow for one retraction, or may have multiple stops to allow for multiple retraction positions. Further, the insertion device and reset mechanism may be constructed such that the headpiece is initially positioned towards the top of the rotatable tabs, and thereby at a later time the patient would rotate the head in a clockwise position to insert the cannula further in to the tissue. View 905 shows the insertion set 900 in a solid view ready to be attached to the patient's skin. It will be understood that the setting mechanism and cannula of FIG. 9 can be constructed and made to cooperate in a way that can change only the depth, change only the position, or change both the depth and position. It will also be understood that the infusion set can easily be modified to insert and reset a biological sensor, such as a sensor for glucose monitoring.

Figure 10:
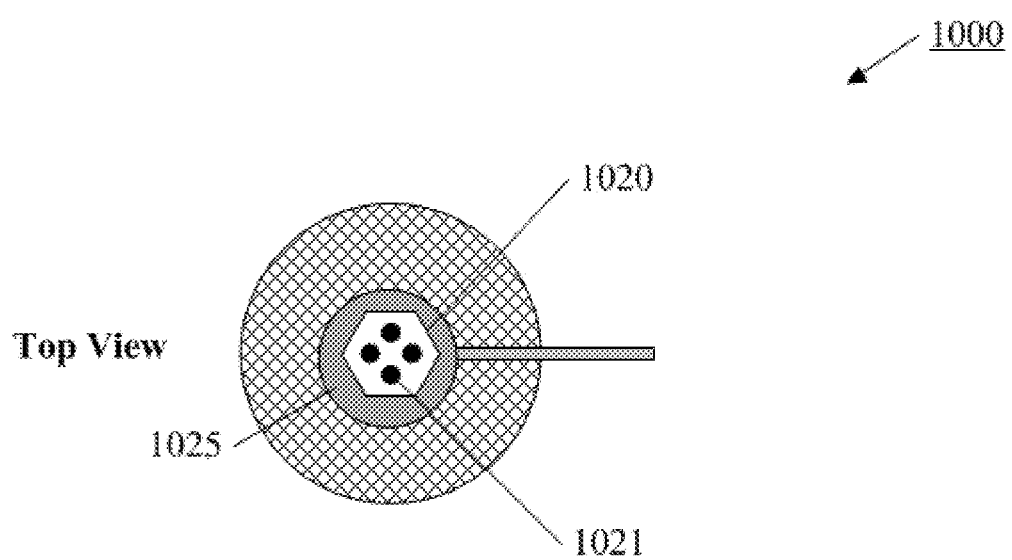
FIG. 10 is an illustration of a top view of an extended use infusion set in accordance with the present invention.

FIG. 10 shows an exemplary embodiment of an infusion set 1000 with multiple ports 1021 in the head 1020 to permit relocation of the straight, curved or helical needle in the same infusion set at the same site, in order to achieve new depots through new insertions. In some cases infusion set 1000 may have a reset mechanism 1025 as described with reference to FIG. 8, and in other cases the reset mechanism 1025 may also include an external setting device (not shown). For example, the patient may use a housing and setting tool to initially insert a cannula to a first depth and location as previously described. When the patient desires to set a new position and location, the patient removes the initially inserted cannula, and then inserts another cannula through one of the other ports 1021. In a alternative use, the patient may remove the cannula from a port, and insert a new cannula into the same port, and use the same insertion point through the skin. However, the new insertion would route to a new position and depth. For example, if the initial cannula went to the left of the port, the new insertion may be to the right of the port, thereby being in new tissue for infusion. In other examples, the new cannula can be selected to insert to a new depth. The initial cannula may be reusable in some circumstances, however, due to the risk of infection, it is more likely that old cannula would be discarded, and a new cannula inserted into a new port. The new cannula would be provided with an associated external setting device including a housing and insertion mechanism that would cooperate with the reset mechanism portion 1025 on the adhesive pad.

The patient would use the external setting device to insert the new cannula into one of the unused ports 1021, and to position the cannula to its therapeutic depth and position. In this way, the new cannula is set to a new depth and position as compared to the original cannula but reuses the same head piece 1020. The patient would then remove the external setting tool. In an alternative use, the patient may remove the cannula from a port, and insert a new cannula into the same port, and use the same insertion point through the skin. However, the new insertion would route to a new position and depth. For example, if the initial cannula went to the left of the port, the new insertion may be to the right of the port, thereby being located in new tissue for infusion. In other examples, the new cannula can be selected to insert to a new depth. Advantageously, the patient does not need to reset the adhesive pad and may use the same general location for a second insertion. Pain and discomfort is decreased, and the cost of inserting a new cannula is substantially reduced as compared to needing a full new insertion set. Additionally, the multiple ports would enable one of the ports to be used for a biological sensor, while another port could be used for infusion. Again, this increases patient comfort while reducing cost.

Although the headpieces are illustrated with 4 ports, it will be understood that more or fewer ports may be provided. For example, as briefly discussed above, a headpiece may be advantageously used having only a single port. That is, a single port can facilitate multiple cannula insertions over a period of time. For example, an initial cannula may be set by the patient through the single port to a particular position and location under the patient's skin. Upon degraded efficacy or a period of time, the patient may remove the first cannula, and insert a new cannula into the same port. In this way, the new cannula is inserted using the same existing insertion point through the skin, thereby reducing insertion force and pain or discomfort to the user. The cannula would be constructed or manipulated to be located at new position and depth different than the initial cannula. This may be accomplished, for example, by providing a set of cannulas, with each cannula designed to insert to a unique position and location. In another example, the set of cannulas may be similar, but have directional indicators that instruct the patient how to position and insert each cannula to assure a new position or depth.

Figure 11A:
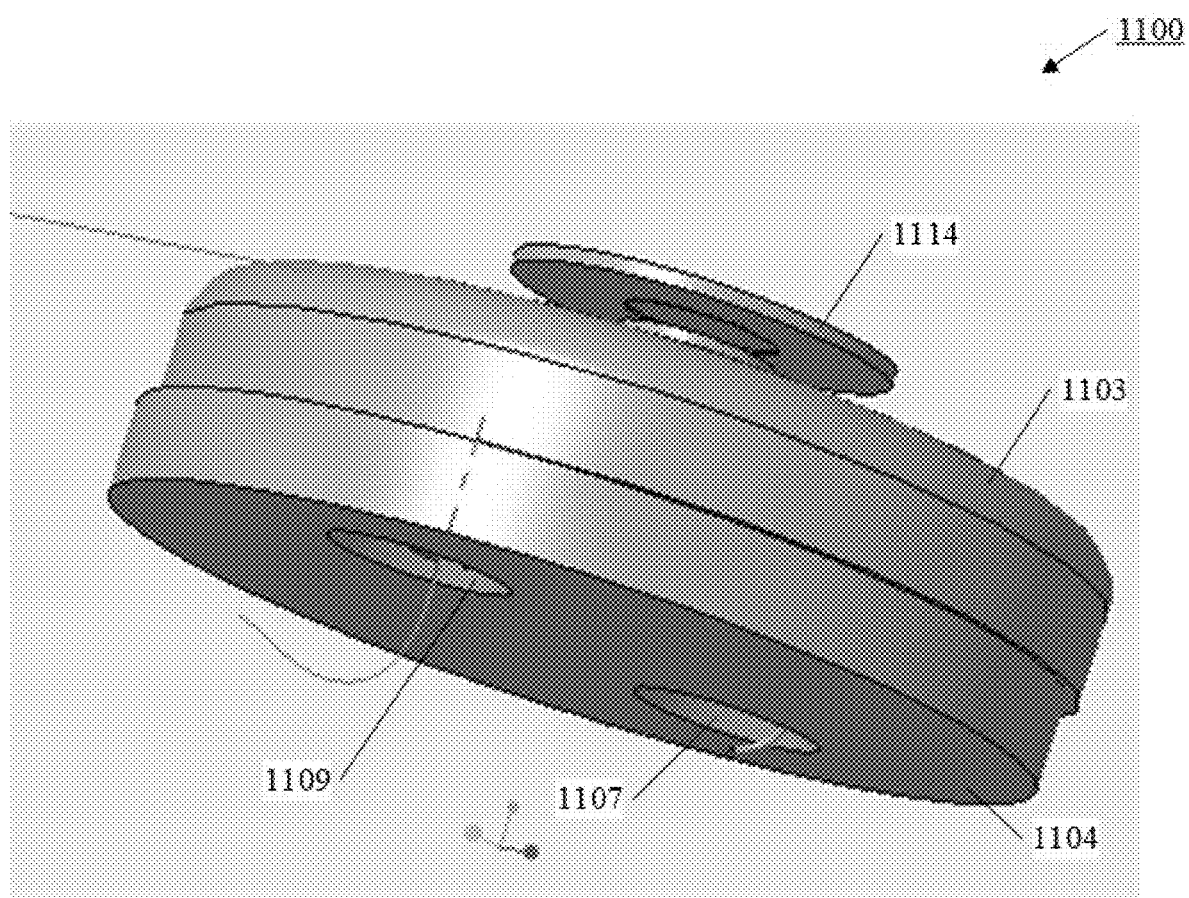
FIGS. 11A and 11B are illustrations of a kinkless infusion set in accordance with the present invention.

Referring now to FIG. 11A, another insertion set 1100 is illustrated. Insertion set 1100 has a multi piece body 1103 that has a base 1104 which typically would include an adhesive pad. This adhesive pad would typically have a removable paper portion that would be removed by the patient, and then the patient would place the base 1104 at a position on his or her body where they would like to do the insertion. Insertion set 1100 is illustrated with bottom openings 1107 and 1109. These bottom openings are where, upon activation by the patient, the introducer needle and cannula are set into a therapeutic position and depth. It will be understood that fewer or more openings may be provided depending upon the number of independently operable cannulas are desired. When the patient has attached the infusion set 1100 to their skin using the adhesive bottom 1104, the patient then exposes a control knob 1114 to begin the setting process. In some cases, the control knob 1114 may be lifted away from the main body 1103, or maybe spring activated, or may have a cover or other seal that the patient would remove. It will be understood that there are many alternatives to the process or technique to expose the control knob 1114. Further, the control knob 1114 is illustrated as being a thin disk. It will be understood that other shapes may be substituted. Once the control knob 1114 is exposed, the patient may activate the control knob 1114 to cause the insertion needle and cannula to be subcutaneously positioned.

Figure 11B:
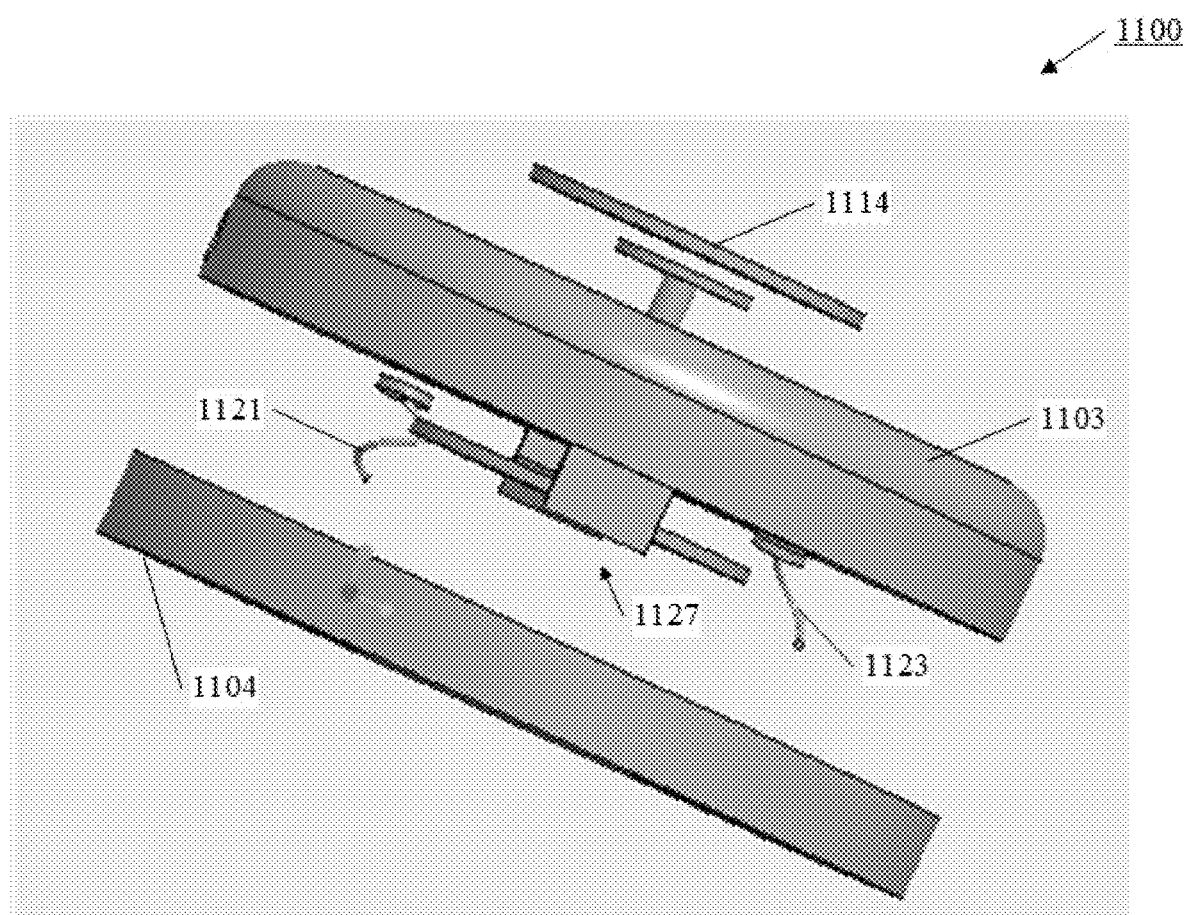

Referring now to FIG. 11B, the insertion set 1100 is shown with the main body 1103 separated from the base portion 1104. In this way, a first cannula 1121 and a second cannula 1123 are exposed for illustration purposes, as well as the mechanical setting structure 1127, which enables a motion made to the control knob 1114 to be translated into a setting motion to set the insertion of needles and cannulas. It will be understood that the infusion set 1100 may be constructed such that both the cannulas 1121 and 1123 are set at the same time. This may be desirable, for example when one of the cannulas is designed for infusing medicine, and the other cannula is set to set a continuous glucose sensor. In other cases, the infusion set 1100 may be designed such that when the control knob 1114 is in one position it sets the cannula 1121, and then at a later time, the control knob 1114 may be used to set the second cannula 1123. In this way, a single infusion set 1100 may be attached to a patient's skin, and multiple infusion sites may be selected for insertion at the same time or for insertion at different times. It will also be understood that the control knob 1114 and mechanical mechanisms 1127 may be used to set each cannula into a first therapeutic depth and position, and then at a later time, reset the cannula to be at a different therapeutic depth and position.

Figure 12A:
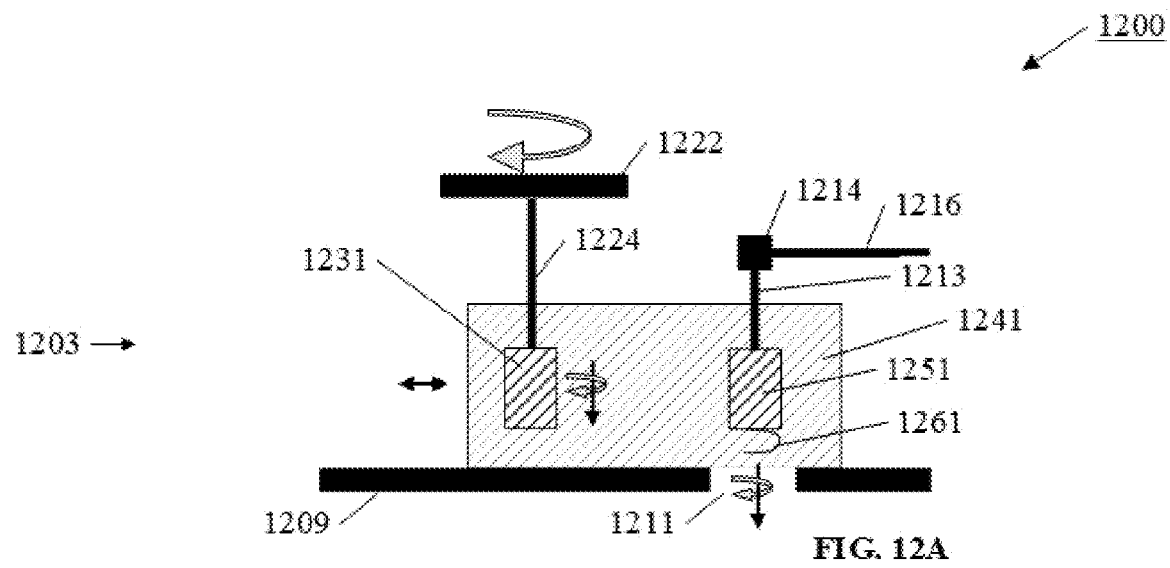
FIGS. 12A, 12B, and 12C are function block diagrams of a kinkless infusion set in accordance with the present invention.
Figure 12B:
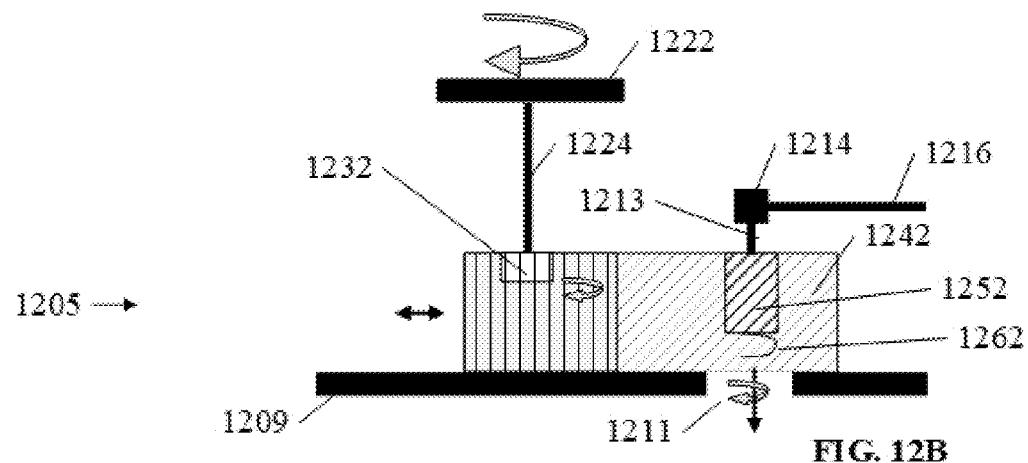
Figure 12C:
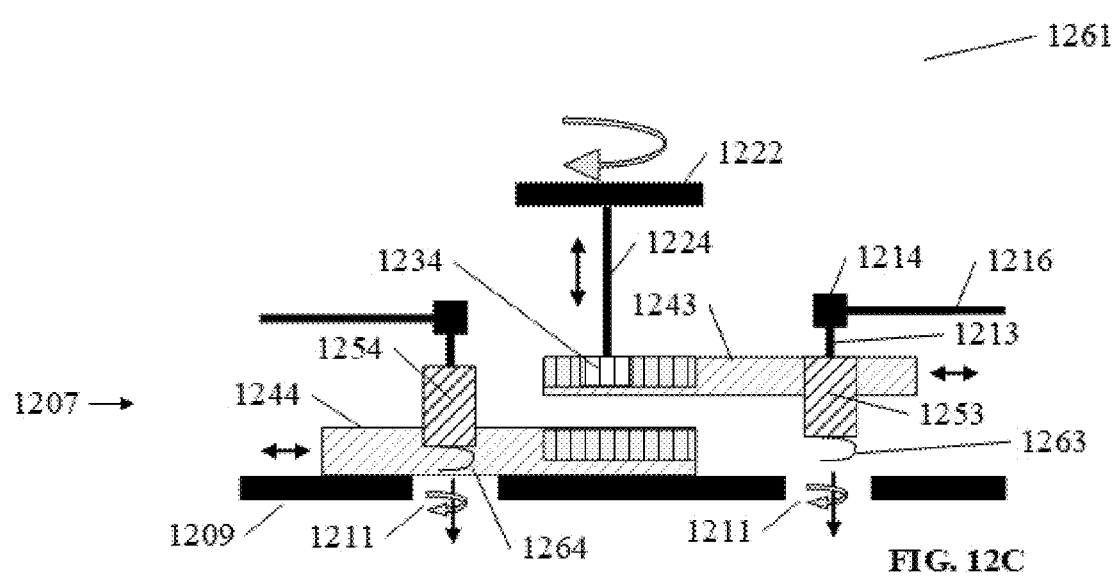

Referring now to FIGS. 12A, 12B and 12C, another infusion set 1200 is generally illustrated. It will be understood that substantial detail for infusion set 1200 is not illustrated so that the inventive features may be more readily described. When practical, the same reference character numbers have been used in the three described embodiments, 1203, 1205 and 1207. Referring now to infusion set 1203, the infusion set 1203 is illustrated with a base 1209 that is intended to be adhered to a patient, for example, using an adhesive pad. The base 1209 may have one or more openings such as opening 1211 through which the insertion needle and cannula will extend and be positioned subcutaneously into the patient. Infusion set 1203 has a control knob 1222 which can be selectively exposed by the patient. For example, the control knob 1222 may pop up, may be spring-loaded, or may be covered with a physical cover or seal that is removed by the patient.

Once the control knob has been exposed, the patient can then engage the control knob 1222, for example by rotating it such that the rotational forces are passed through rod 1224 to gear 1231. Gear 1231 has teeth set at a bias to engage cooperating teeth in a slidable rack 1241. In this way, the gear 1231 and the rack 1241 create what is generally referred to as a rack and pinion system. More particularly, when the patient rotates the control knob 1222, the gear 1231 is likewise rotated, causing the rack 1241 to translate in a direction parallel to the base plate 1209. It will be understood that the infusion device 1203 may be constructed in a way that the rack 1241 may only move in one direction, and in other cases may allow for bidirectional motion of the rack 1241. As the teeth in gear 1231 are biased in the same direction as the teeth in rack 1241, the gear 1231, rod 1224, and control knob 1222 will also be moved in a direction towards the base 1209.

The rack 1241 also interacts with a second gear 1251, which also has similarly biased teeth. Accordingly, when the rack 1241 moves, it causes the gear 1251 to rotate and also be driven towards the base plate 1209. Infusion tube 1216 is used to supply medicine when the cannula has been properly positioned subcutaneously. Infusion tube 1216 couples to a junction 1214 which enables tub 1213 to rotate, yet be sealingly connected to infusion tube 1216 such that medicine may flow through tube 1216, through tube 1213, into cannula 1261 and then be infused into the patient. It will be understood that several types of sealing and rotating junctions are available for use.

In operation, the patient engages the control knob 1222 and rotates it in a way that causes the gear 1251 to also rotate and be driven in a downward direction. Accordingly, the helical cannula (or introducer needle) first pierces the patient's skin, and then is rotated and lowered to its proper position and location. Due to the helical nature of the cannula 1261, the cannula may be inserted relatively shallow beneath the skin, for example 3 mm to 5 mm, and thereby be positioned relatively horizontal to the surface of the patient's skin. By enabling a shallower insertion, patient comfort is increased, and efficacy of the medication is also increased. It will be understood that the helical cannula may have end ports, as well as side ports that can facilitate delivery of medicine over a larger subcutaneous physical area.

It will be understood that in some cases the control knob may be reversible, such that the gear 1251 may be used to extract some or all of the cannula system. For example, it may be configured such that it may extract an introducer needle. It will also be understood that infusion set 1203 may be constructed such that the cannula 1261 may be set to a first position on location for infusion, then at a later time, reset to a new position on location, thereby increasing the length of time that the infusion set 1203 can be used between replacements.

Infusion set 1205 is similar to infusion set 1203, so only differences will be described. In infusion set 1205, the rack 1242 has two different teeth structures. First, gear 1232, which is coupled to the control knob 1222 through rod 1224 has vertically aligned teeth. Accordingly, that portion of the rack 1242 has mating vertically aligned teeth. In this way, rotating the control knob 1222 causes the rack 1242 to move parallel to the base 1209, but does not cause the gear 1232 to have any motion perpendicular to the base 1209. However, the rack 1242 has gear 1252 with its teeth on a bias, and that portion of the rack 1242 also has its teeth on a complementary bias. Accordingly, as the rack 1242 translates parallel to the base 1209, the cannula 1262 is rotated and moved toward the base 1209, then continues to rotate to pierce the patient's skin, and then rotates the cannula 1262 subcutaneously in the patient until the cannula 1262 is set at the desired depth and location. As described with reference to 1203, the cannula may be advantageously set 3 mm to 5 mm below the surface, and have both end ports and side ports for effective delivery of medication.

Infusion set 1207 is similar to infusion set 1205, except infusion set 1207 is constructed to have multiple cannulas that may be independently driven. In this regard, as with infusion set 1205, the infusion set 1207 has a control knob that moves a gear 1234 through rod 1224. The teeth in gear 1234 are vertically aligned, as are the teeth on a portion of rack 1243. As the patient rotates the control wheel 1222, the rack 1243 translates parallel to the base 1209, thereby rotating and driving downward the gear 1253, which likewise drives downward and sets cannula 1263 subcutaneously into the patient.

At a later time, the patient sets the control knob 1222 to engage the rack 1244, for example by pushing the rod 1224 towards the rack 1244 such that the gear 1234 engages the vertically tooth section of rack 1244. Now, when the patient rotates control knob 1222, the gear 1234 causes rack 1244 to translate parallel to base 1209. In this way, gear 1254 is engaged to the biased teeth on rack 1244 and so is rotated and pushed toward the base 1209. In this way, gear 1264 is rotated and driven towards the patient's skin, such that the cannula 1264 first pierces the skin, and is then set 3 mm to 5 mm under the patient's skin.

Figure 13A:
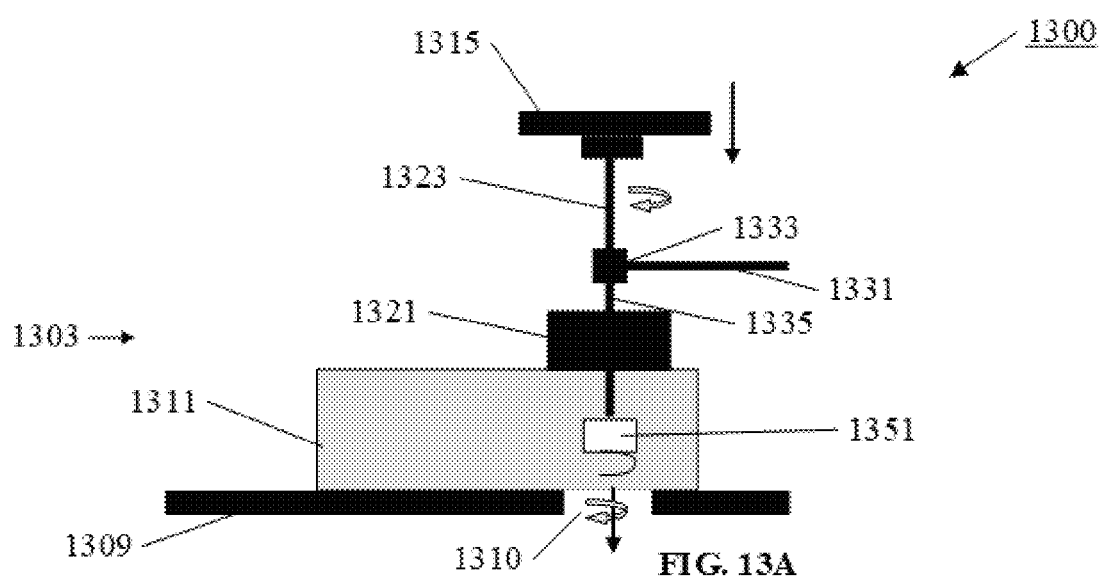
FIGS. 13A and 13B are function block diagrams of a kinkless infusion set in accordance with the present invention.
Figure 13B:
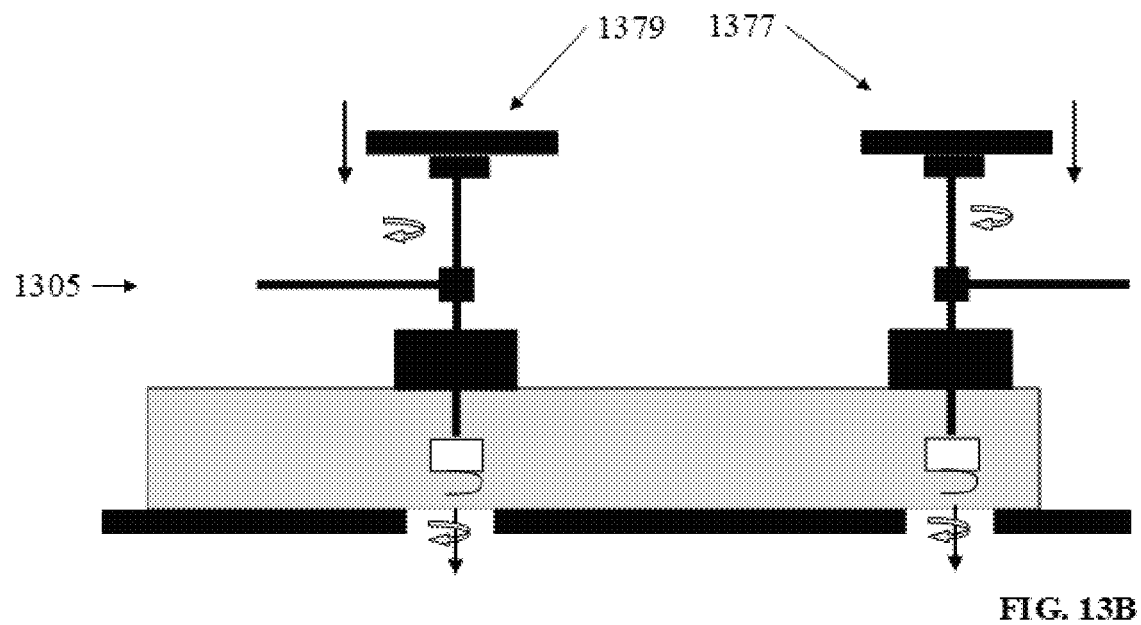

Referring now to FIGS. 13A and 13B, and alternative infusion set 1300 is illustrated. Infusion set 1303 has a base 1309 that may be adhered to a patient's skin, for example, using an adhesive pad. The base 1309 has an opening 1310 through which the cannula 1351 may be driven. A stabilizing structure 1311 sits on top of base 1309, which in turn supports a collar 1321. Collar 1321 does not move, but has an internal threading that cooperates with external threading on rod 1335. These cooperating threads are sized and shaped such that when the rod 1335 moves through the collar 1331, the rod 1335 rotates. An infusion tube 1331 connects to a junction 1333 such that the fluid medicine may flow from tube 1331 into tube 1335 and into cannula 1351. After the patient has exposed the control knob 1315, the patient is able to push down the control knob 1315 through rod 1323 such that the rod 1335 is rotated within collar 1321, providing the rotational motion needed to rotate the cannula 1351 in its helical insertion path. Thereby, it is a combination of the patient's downward push on rod 1315 that causes the cannula 1351 to move in a direction towards base 1309, and the cooperating threading between the collar 1321 and rod 1335 causes the cannula 1351 to rotate at a proper and related speed. In this way, the cannula is pushed toward and into the patient's skin, and rotates and lowers until the cannula is positioned 3 mm to 5 mm below the surface of the skin. The cannula 1351 may have end and side ports for efficient delivery of medication over a wider subcutaneous area.

As to infusion set 1305, the setting structure 1377 is the same as that set out for infusion set 1303, so will not be described in detail. In a similar manner setting structure 1379 is similar to setting structure 1377, however setting structure 1379 is constructed so that the infusion tub extends in a different direction. In this way, infusion set 1305 has multiple setting structures that may be extended through a single base. Although setting structure 1305 is illustrated with two such setting structures, it will be appreciated that more setting structures may be used.

Figure 14:
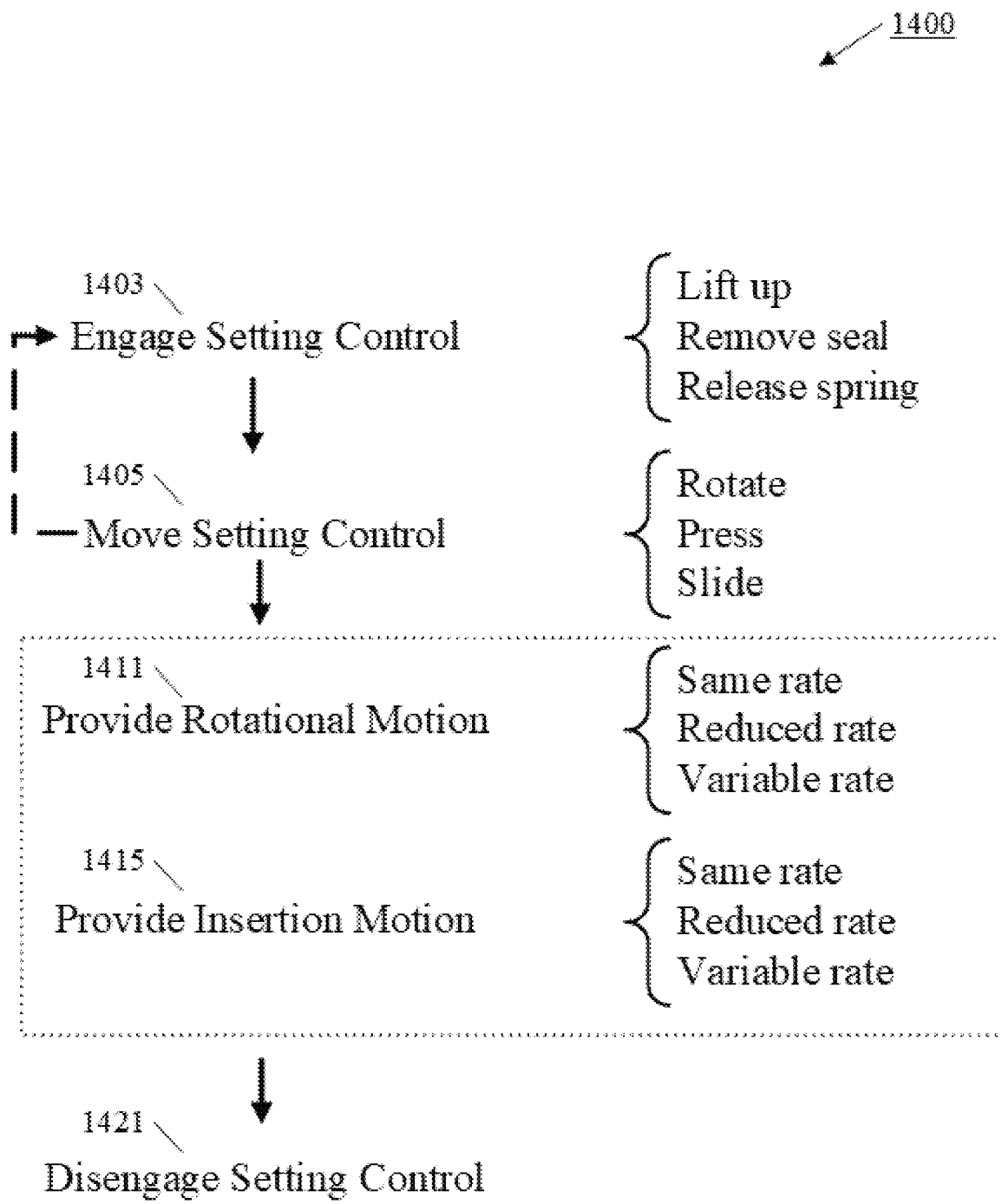
FIG. 14 is a flowchart of a method or using a kinkless infusion set in accordance with the present invention.

Referring now to FIG. 14, a method 1400 is illustrated for using an infusion set in accordance with the present invention. As shown at 1403, the user first engages the setting control. For example, the user may lift up the setting control, remove a seal to expose setting control, or may have some sort of spring release system for exposing the setting control. It will be appreciated that there are many ways that a patient may be able to expose the setting control from the body of the infusion set.

In step 1405, the patient moves the setting control with the intention to begin the cannula setting process. For example, in some cases the patient may be able to rotate the setting control in one or two directions, the patient may press or lift the setting control, and in other cases the setting control may be constructed for the patient to slide in one or two dimensions. As described earlier, this movement of the setting control then provides rotational and insertion motions that is used to set the cannula.

As shown in block 1411 the movement of the setting control is used to provide both a rotational motion and an insertion motion 1415 for setting the cannula. In some cases, the rotational motion may be at the same rate as the movement of the setting control, and in other cases the setting control may be geared to provide a reduced rate of rotation as compared to the rate of rotation of the setting control. In this way, for example, a user would be able to spin the setting control at a relatively fast rate, and yet have the rotation of the setting device be at a slower, less painful rate. In other cases, the setting control could be done at a variable rate. For example, the setting control could rotate the cannula rather rapidly from its storage position to the surface of the skin, and then be geared in such a way that the setting control slows down during the actual piercing and positioning process. In a similar manner, the insertion motion, which is driving the cannula towards the base of the infusion set and towards the patient's skin, may also provide for the downward motion to be at the same rate as the setting control, at a reduced rate, or at a variable rate. It will be understood that there can be many relationships between the motion of the setting control and the rotational and downward insertion motion for the actual setting device.

Figure 15:
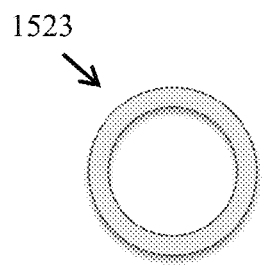
FIG. 15 has an illustration of a simple circular cross-section for rigid needle or flexible, kinkless cannula for an extended use infusion set in accordance with the present invention.

Referring now to FIG. 15, an infusion set rigid needle or flexible, kinkless cannula 1523 with circular cross-section is illustrated. Upon insertion of the needle, or insertion of the cannula with an introducer needle, the latter of which is subsequently removed, fluid will flow through the center of this needle or cannula to the tip or to one or more side ports out into the surrounding subcutaneous tissue. This cross-section is applicable to straight, curved, or helical cannula. Material selection for the cannula will be of a higher modulus of elasticity than currently available cannulas to increase structural integrity of the cannula to prevent kinking or other deformation or blocking of the cannula that may reduce or obstruct fluid flow.

Figure 16:
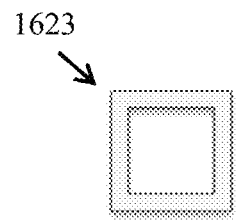
FIG. 16 is an illustration of a box cross-section for rigid needle or flexible, kinkless cannula for use with the extended use infusion set in accordance with the present invention.

Referring now to FIG. 16, an infusion set rigid needle or flexible, kinkless cannula 1623 with box cross-section is illustrated. Upon insertion of the needle, or insertion of the cannula with an introducer needle, the latter of which is subsequently removed, fluid will flow through the center of this needle or cannula to the tip or to one or more side ports out into the surrounding subcutaneous tissue. This cross-section is applicable to straight or curved cannula. Material selection for the cannula will be of a higher modulus of elasticity than currently available cannulas to increase structural integrity of the cannula to prevent kinking or other deformation or blocking of the cannula that may reduce or obstruct fluid flow.

Figure 17:
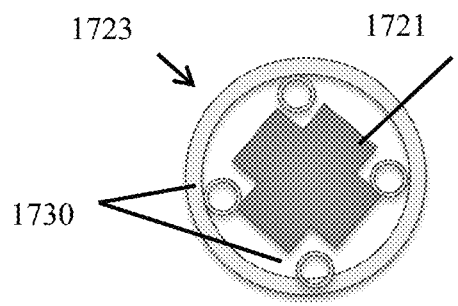
FIG. 17 is an illustration of a flexible, kinkless cannula with circular cross-section with hollow, gas-filled or fluid filled tubing for reinforcement and notched introducer needle shown for an extended use infusion set in accordance with the present invention.

Referring now to FIG. 17, an infusion set flexible, kinkless cannula 1723 with circular cross-section and hollow, gas-filled or fluid-filled internal tubes 1730 is illustrated. Introducer needle 1721, which is removed after positioning the cannula is also illustrated in cross-section. This cross-section is applicable to straight, curved, or helical cannula. Internal tubes 1730 may be sealed and filled with gas at ambient or above ambient pressure, or may not be sealed. Tubes may be straight down the length of the cannula, or may spiral down the inside circumference. Internal tubes may be constructed such that they fill with fluid when medicine is introduced from the infusion pump. In this way, the internal tubes will increase structural integrity of the cannula to prevent kinking or other deformation or blocking of the cannula that may reduce or obstruct fluid flow. Material selection for the cannula may also be of a higher modulus of elasticity than currently available cannula to further increase structural integrity of the cannula. Internal tubes may also have openings to side ports to allow medicine to exit the cannula at 1-4 locations other than the cannula tip. These side ports may have flow-controlling orifices or be free-flowing. Flow-controlling orifices may increase internal pressure to increase structural contribution or may be used to determine how much fluid flows out each port, or both.

Figure 18:
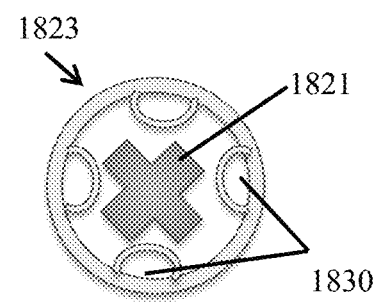
FIG. 18 is an illustration of a flexible, kinkless cannula with circular cross-section with hollow, gas-filled or fluid-filled channels for reinforcement and notched introducer needle shown for an extended use infusion set in accordance with the present invention.

Referring now to FIG. 18, an infusion set flexible, kinkless cannula 1823 with circular cross-section and hollow, gas-filled or fluid-filled internal tubes 1830 is illustrated. Introducer needle 1821, which is removed after positioning the cannula is also illustrated in cross-section. This cross-section is applicable to straight, curved, or helical cannula. Internal tubes 1830 may be sealed and filled with gas at ambient or above ambient pressure, or may not be sealed. Tubes may be straight down the length of the cannula, or may spiral down the inside circumference. Internal tubes may be constructed such that they fill with fluid when medicine is introduced from the infusion pump. In this way, the internal tubes will increase structural integrity of the cannula to prevent kinking or other deformation or blocking of the cannula that may reduce or obstruct fluid flow. Material selection for the cannula may also be of a higher modulus of elasticity than currently available cannula to further increase structural integrity of the cannula. Internal tubes may also have openings to side ports to allow medicine to exit the cannula at 1-4 locations other than the cannula tip. These side ports may have flow-controlling orifices or be free-flowing. Flow-controlling orifices may increase internal pressure to increase structural contribution or may be used to determine how much fluid flows out each port, or both.

Figure 19:
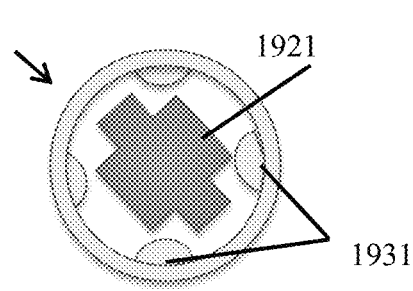
FIG. 19 is an illustration of a flexible, kinkless cannula with circular cross-section with solid ribs made from the same or material as the cannula or different material and notched introducer needle shown in accordance with the present invention.

Referring now to FIG. 19, an infusion set flexible, kinkless cannula 1923 with circular cross-section and solid ribs 1931 is illustrated. The solid ribs may be extruded from the same material as the cannula, or may be of a different material and constructed after the original cannula extrusion. This cross-section is applicable to straight, curved, or helical cannula. Ribs may be straight down the length of the cannula, or may spiral down the inside circumference. In this way, the internal rib structures will increase structural integrity of the cannula to prevent kinking or other deformation or blocking of the cannula that may reduce or obstruct fluid flow. Material selection for the cannula may also be of a higher modulus of elasticity than currently available cannula to further increase structural integrity of the cannula.

Figure 20:
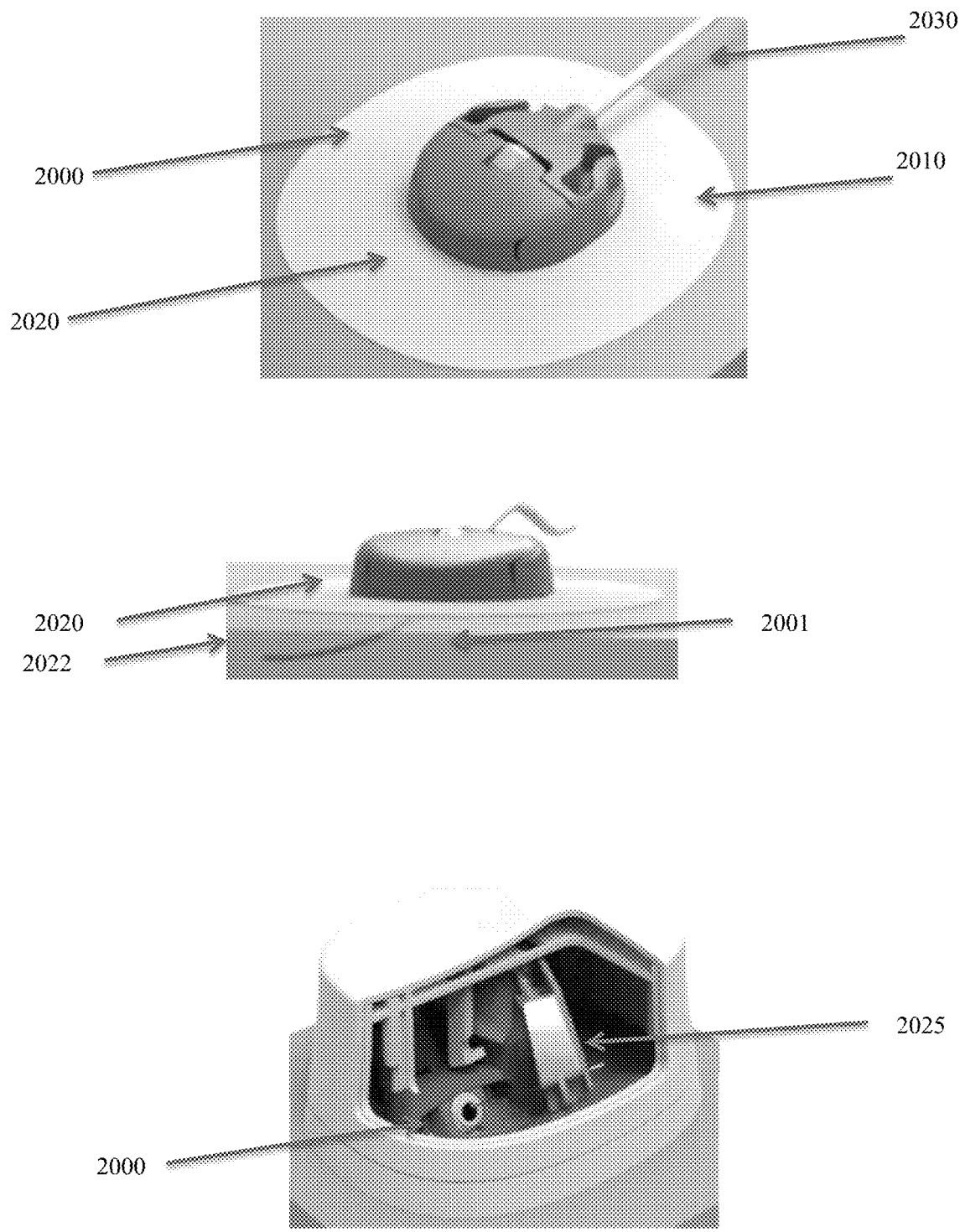
FIG. 20 has illustrations of a partial 3-D view showing an extended use infusion set in operation and being inserted and in accordance with the present invention.

Referring now to FIG. 20, an infusion set with one example of the cannula 2001 connected to the head 2020. As can be seen, the needle 2001 is curved, and constructed of a metal material. It will be understood that the cannula 2001 can be constructed from several different materials, including combinations of materials (e.g., metal and plastic/polymeric), and may be made with different curves, lengths, and thicknesses. Infusion set 2000 is also adhered to the human body with adhesive contact 2010 and has a head 2020 which allows medication to be injected through a tube 2030. In some cases infusion set 2000 may have a reset mechanism 2025 as described with reference to FIG. 8, and in other cases the reset mechanism 2025 may also include an external setting device (as shown).

While particular preferred and alternative embodiments of the present intention have been disclosed, it will be appreciated that many various modifications and extensions of the above described technology may be implemented using the teaching of this invention. All such modifications and extensions are intended to be included within the true spirit and scope of the appended claims.

What is claimed is:

1. An infusion set, comprising:
    a base constructed to be attached to a patient's skin;
    a body storing a curved or helical cannula;
    a control knob that is operably connected the curved or helical cannula;
    a rack and pinon structure operably coupling the control knob to the curved or helical cannula; and
    wherein the control knob is engageable by the patient to simultaneously rotate the curved or helical cannula and move the curved or helical cannula from the body to the skin such that the cannula is substantially kink free as it rotates under the patient's skin.

2. The infusion set according to claim 1, wherein the patient engages the control knob to simultaneously rotate the curved or helical cannula and move the cannula from the body to a subcutaneous depth of between 3 mm and 5 mm.

3. The infusion set according to claim 1, the curved or helical cannula further comprising side ports.

4. The infusion set according to claim 1, the curved or helical cannula shaped to rotate into a subcutaneous depth of between 3 mm and 5 mm.

5. The infusion set according to claim 1, wherein the control knob is constructed to be rotated.

6. The infusion set according to claim 1, wherein the cannula has inner tubing chambers which may be filled with gas or fluid at or above ambient pressure.

7. The infusion set according to claim 6, wherein one or more of the inner tubing chambers may allow fluid to pass through sides of the cannula, rather than allowing fluid to reenter a main cannula chamber.

8. The infusion set according to claim 7, wherein one or more of the inner tubing chambers may allow fluid to pass through flow-controlling orifices of precise diameter to increase pressure within the chamber to contribute to the structural integrity of the cannula.

9. The infusion set according to claim 7, wherein one or more of the inner tubing chambers may allow fluid to pass through flow-controlling orifices of precise diameter to increase pressure within the chamber to determine the proportion of flow that passes through each port.

10. An infusion set, comprising:
    a base constructed to be attached to a patient's skin;
    a body storing a curved or helical cannula;
    a control knob that is operably connected the curved or helical cannula;
    a rack that engages a first gear that is directly connected to the control knob, and where a second gear that is directly connected to the curved or helical cannula engages the rack; and
    wherein the control knob is engageable by the patient to simultaneously rotate the curved or helical cannula and move the curved or helical cannula from the body to the skin such that the cannula is substantially kink free as it rotates under the patient's skin.

11. The infusion set according to claim 10, wherein the patient engages the control knob to simultaneously rotate the curved or helical cannula and move the cannula from the-body to a subcutaneous depth of between 3 mm and 5 mm.

12. The infusion set according to claim 10, the curved or helical cannula further comprising side ports.

13. The infusion set according to claim 10, wherein the control knob is constructed to be rotated.

14. The infusion set according to claim 10, wherein the cannula has inner tubing chambers which may be filled with gas or fluid at or above ambient pressure.

15. An infusion set, comprising:
    a base constructed to be attached to a patient's skin;
    a body storing a curved or helical cannula;
    a control knob that is operably connected the curved or helical cannula;
    variable gearing constructed so that a constant motion applied to the control knob causes the curved or helical cannula to move and rotate more slowly as the patient continues to move the control knob and wherein the control knob is engageable by the patient to simultaneously rotate the curved or helical cannula and move the curved or helical cannula from the body to the skin such that the cannula is substantially kink free as it rotates under the patient's skin.

16. The infusion set according to claim 10, wherein the first gear and the second gear have teeth at a different bias, and the rack has a first portion to engage the first gear and a second portion to engage the second gear.

17. The infusion set according to claim 15, wherein the patient engages the control knob to simultaneously rotate the curved or helical cannula and move the cannula from the-body to a subcutaneous depth of between 3 mm and 5 mm.

18. The infusion set according to claim 15, the curved or helical cannula further comprising side ports.

19. The infusion set according to claim 15, wherein the control knob is constructed to be rotated.

20. The infusion set according to claim 15, wherein the cannula has inner tubing chambers which may be filled with gas or fluid at or above ambient pressure.

* * * * *